(12) United States Patent
Oepen et al.

(10) Patent No.: US 8,900,286 B2
(45) Date of Patent: Dec. 2, 2014

(54) MEDICAL DEVICE SHIELD AND METHODS FOR DELIVERING A MEDICAL DEVICE

(75) Inventors: Randolf von Oepen, Los Altos Hills, CA (US); Travis R. Yribarren, Campbell, CA (US); Alex D. Alviar, Woodside, CA (US); Barbara E. Stamberg, San Jose, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 230 days.

(21) Appl. No.: 13/037,008

(22) Filed: Feb. 28, 2011

(65) Prior Publication Data

US 2011/0213451 A1  Sep. 1, 2011

Related U.S. Application Data

(60) Provisional application No. 61/309,359, filed on Mar. 1, 2010, provisional application No. 61/348,597, filed on May 26, 2010.

(51) Int. Cl.
| | |
|---|---|
| *A61F 2/06* | (2013.01) |
| *A61F 2/00* | (2006.01) |
| *A61F 2/958* | (2013.01) |
| *A61F 2/966* | (2013.01) |
| *A61F 2/95* | (2013.01) |

(52) U.S. Cl.
CPC ....... *A61F 2/0095* (2013.01); *A61F 2002/9583* (2013.01); *A61F 2002/9665* (2013.01); *A61F 2002/9505* (2013.01)
USPC ............................................. 623/1.11; 600/3

(58) Field of Classification Search
CPC ........... A61F 2/0095; A61F 2002/9505; A61F 2002/9583; A61F 2002/9665
USPC .............. 623/1.11, 1.23; 206/363, 349; 600/3
See application file for complete search history.

(56) References Cited

U.S. PATENT DOCUMENTS

| | | | |
|---|---|---|---|
| 5,453,090 A | 9/1995 | Martinez et al. | |
| 5,605,530 A * | 2/1997 | Fischell et al. ..................... | 600/3 |
| 5,824,041 A | 10/1998 | Lenker et al. | |
| 6,090,035 A * | 7/2000 | Campbell et al. ................. | 600/7 |
| 6,110,146 A | 8/2000 | Berthiaume et al. | |
| 6,132,358 A * | 10/2000 | Glenn et al. ...................... | 600/3 |
| 6,749,584 B2 | 6/2004 | Briggs et al. | |
| 7,462,191 B2 | 12/2008 | Spenser et al. | |

(Continued)

FOREIGN PATENT DOCUMENTS

| | | |
|---|---|---|
| EP | 0867156 | 9/1998 |
| EP | 0916318 | 5/1999 |

(Continued)

OTHER PUBLICATIONS

U.S. Appl. No. 13/220,123, Dec. 7, 2012, Office Action.

(Continued)

*Primary Examiner* — Darwin Erezo
*Assistant Examiner* — Martin T Ton
(74) *Attorney, Agent, or Firm* — Workman Nydegger; Jonathan Feuchtwang

(57) ABSTRACT

Device shields for packaging and protecting medical devices during storage and deployment. A device shield includes a housing configured to maintain a medical device and at least a portion of a medical device delivery apparatus within the housing, and a limit element having a first constraining position and a second open position.

23 Claims, 24 Drawing Sheets

(56) References Cited

U.S. PATENT DOCUMENTS

| | | |
|---|---|---|
| 7,785,361 B2 * | 8/2010 | Nikolchev et al. ............ 623/1.11 |
| 2003/0060876 A1 | 3/2003 | Loshakove et al. |
| 2003/0114910 A1 | 6/2003 | Juhani Laakso et al. |
| 2004/0059348 A1 | 3/2004 | Geske et al. |
| 2005/0154441 A1 * | 7/2005 | Schaeffer et al. ............ 623/1.11 |
| 2005/0218022 A1 | 10/2005 | Cervantes |
| 2006/0015167 A1 | 1/2006 | Armstrong et al. |
| 2011/0208292 A1 * | 8/2011 | Von Oepen et al. ......... 623/1.23 |

FOREIGN PATENT DOCUMENTS

| | | |
|---|---|---|
| EP | 1078611 | 2/2001 |
| WO | WO 99/53864 | 10/1999 |
| WO | WO 2005/107646 | 11/2005 |
| WO | WO 2006/073745 | 7/2006 |
| WO | WO 2008/045156 | 4/2008 |

OTHER PUBLICATIONS

U.S. Appl. No. 61/309,359, filed Mar. 1, 2010, Oepen et al.
U.S. Appl. No. 61/348,597, filed May 26, 2010, Oepen et al.
U.S. Appl. No. 13/220,123, filed Aug. 29, 2011, Von Oepen et al.
U.S. Appl. No. 13/220,123, Jun. 4, 2013, Office Action.

* cited by examiner

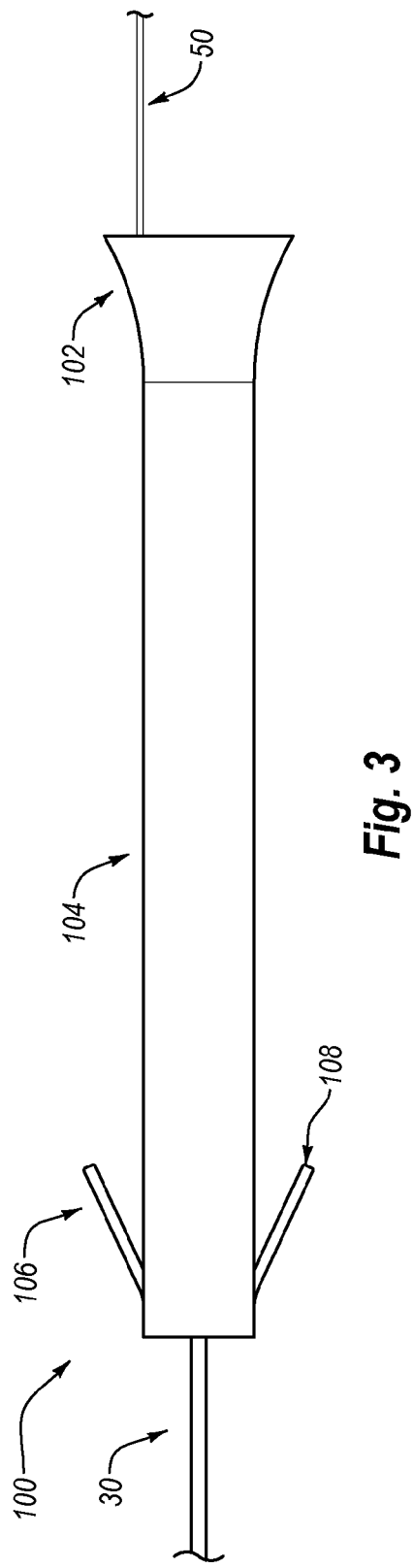
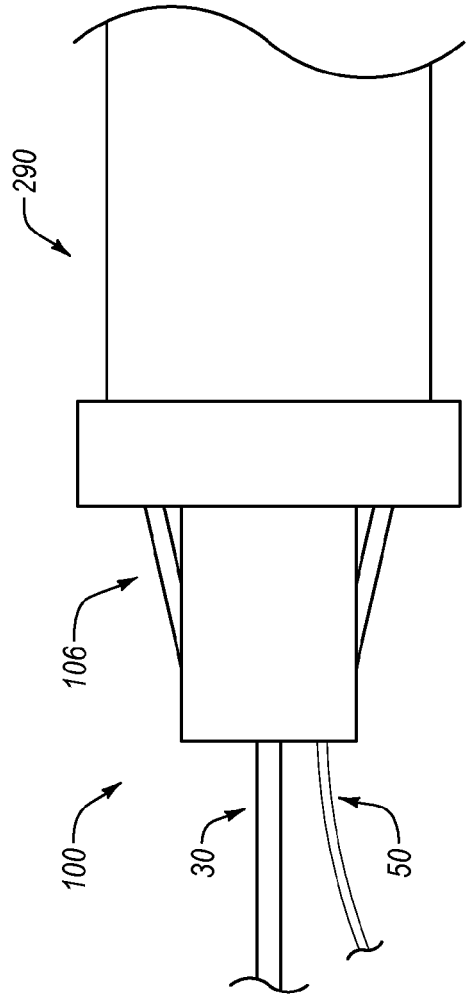

MEDICAL DEVICE SHIELD AND METHODS FOR DELIVERING A MEDICAL DEVICE

CROSS-REFERENCE TO RELATED APPLICATIONS

This Application claims the benefit of and priority to U.S. Provisional App. Ser. No. 61/309,359, filed 1 Mar. 2010, entitled SYSTEMS AND METHODS FOR LOADING A GUIDE WIRE, and U.S. Provisional App. Ser. No. 61/348,597, filed May 26, 2010, entitled SYSTEMS AND METHODS FOR LOADING A GUIDE WIRE, the entirety of each of which is incorporated herein by reference.

BACKGROUND

1. The Field of the Invention

The present disclosure relates to various medical devices deliverable and deployable within a lumen. More particularly, the invention relates to devices for shielding a medical device and methods for delivering a medical device into a subject's body while minimizing or preventing contamination of or damage to the medical device.

2. The Relevant Technology

Stents, grafts, and a variety of other endoprostheses are used in interventional procedures, such as for treating aneurysms, lining or repairing vessel walls, filtering or controlling fluid flow, and expanding or scaffolding occluded or collapsed vessels. Such endoprostheses may be delivered and used in virtually any accessible body lumen of a human or animal, and may be deployed by any of a variety of recognized means. One recognized use for a vascular endoprosthesis is for the treatment of atherosclerotic stenosis in blood vessels. For example, after a patient undergoes a percutaneous transluminal coronary angioplasty, or similar interventional procedure, a stent is often deployed at the treatment site to improve the results of the medical procedure and reduce the likelihood of restenosis.

Typically, a vascular endoprosthesis, such as a stent, is delivered by a delivery sheath, such as a catheter, to a desired location or deployment site inside a body lumen or other tubular organ. In order to deliver a stent or other medical device to a desired location, a guide wire or other device may be used to add steering and support. The guide wire is generally threaded through and/or over the delivery system. Therefore, systems and methods for loading a guide wire may be desirable.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments disclosed herein relate to medical devices and in particular to device shields and methods of use.

The present disclosure is related to protective covers or device shields for packaging and protecting medical devices (e.g., stents, filters, shunts, other implantable devices, or other medical devices) during storage and deployment. Stent retention, surface integrity, and crossing profile are exemplary characteristics of a stent or another medical device that may be important to positive clinical outcomes. At least one of these characteristics may be positively impacted by at least one of the embodiments of a device shield disclosed herein.

For example, a device shield may constrain the dimensions of the stent and/or balloon during the storage process and/or at least a portion of the delivery process, which may impact the overall profile and/or stent retention by limiting expansion during storage. It may be possible for a stent and/or balloon to expand slightly during storage due to residual stresses and/or fluctuations in humidity and/or temperature. Even slight expansions of the stent may negatively affect stent retention and/or crossing profile.

Furthermore, a device shield may reduce or prevent the adhesion of free particulates in the surrounding environment or on a surgeon's gloves from contacting a sensitive area of the medical device (e.g. the stent, filter, or other implantable device, or other medical device) and/or the delivery device (e.g. the balloon catheter or other delivery device). Without a device shield, a guide wire or other delivery device may scratch the medical device and/or contaminants may deposit on the medical device. Either of these events may adversely impact product performance and/or clinical outcome.

In one embodiment, a device shield is described. The device shield includes a housing configured to maintain a medical device and at least a portion of a medical device delivery apparatus within the housing and a limit element having a first position and a second position. The first position of the limit element is configured to constrain the medical device relative to the housing, and the second position is configured to permit movement of the medical device relative to the housing.

The device shield may provide at least one of the following: easier guide wire insertion into a catheter lumen, minimization of surface damage of the stent and/or balloon before and/or during guide wire loading, maintaining the stent and/or balloon in a pre-deployed configuration, minimizing contamination of the stent and/or balloon surfaces before insertion into a patient, facilitating insertion into an access device, simplifying removal of the loading device, restraining the loading device from insertion into a patient's anatomy, insertion without a need for removal of the sheath in a separate step, or combinations thereof.

In another embodiment, a device shield for a medical device is disclosed. The device shield includes a molded housing configured to maintain a medical device and at least a portion of a medical device delivery apparatus associated with the medical device within the housing, a limit element configured to constrain the medical device and/or the portion of a medical device delivery apparatus associated with the medical device in at least one dimension, a retaining member slidably associated with the housing and configured to maintain the limit element in the first position, and an outlet configured for introducing the medical device into a body of a patient.

In yet another embodiment, a kit is disclosed. The kit includes a device shield that includes a housing configured to maintain a medical device and at least a portion of a medical device delivery apparatus associated with the medical device, and a limit element configured to constrain the medical device and/or the portion of the medical device delivery apparatus associated with the medical device in the housing in at least one dimension. The kit further includes a medical device and a medical device delivery apparatus.

In still yet another embodiment, a method for delivering a medical device into a patient body is disclosed. The method includes (1) positioning an introducer apparatus in the patient body and (2) positioning at least a portion of a device shield into the introducer apparatus. In one embodiment, the device shield includes (a) a housing that includes a medical device and at least a portion of a medical device delivery apparatus associated with the medical device, and (b) a limit element having a first position configured to constrain the medical device and/or the portion of the medical device delivery apparatus associated with the medical device. The method further includes (3) transitioning the limit element to a second position, wherein the second position is configured to permit delivery of the medical device into the patient body, and (4) delivering the medical device from the device shield and into the patient body via the introducer apparatus.

In a further embodiment, a device shield includes an expanded portion, a storage portion, and a magnification portion. The expanded portion directs a guide wire into a guide wire lumen of a medical device that is disposed within the device shield. The storage portion is adapted to have the medical device disposed therein. The magnification element enables magnified visual inspection of the medical device disposed within the storage portion. In one embodiment, the magnification element is a lens that is overmolded or attached to a portion of the device shield to provide visual access to the storage portion and the medical device disposed therein. In another embodiment, the magnification element is formed of a transparent material having a convex shape.

In still another exemplary embodiment, a device shield includes an inner sheath and an outer sheath. The inner sheath at least partially defines a storage portion configured to have a medical device disposed therein. The inner sheath also has a distal end that can be (1) compressed to form a lumen for receiving a guide wire therethrough, and (2) expanded to enable deployment of the medical device out of the storage portion. The outer sheath is disposed at least partially about the inner sheath.

The outer sheath is adapted to compress the distal end of the inner sheath and allow for expansion of the distal end of the inner sheath. In one embodiment, the distal end of the inner sheath includes a plurality of flex sections that can be flexed inward toward a central axis of the inner sheath such that the plurality of flex sections form a tapered lumen configured to direct a guide wire into the guide wire lumen of the medical device. The plurality of flex sections may naturally flex away from the central axis of the inner sheath to cause the lumen to be large enough for the medical device to pass therethrough.

In other embodiments, the outer sheath is adapted to move between a first position and a second position along the length of the inner sheath. The outer sheath may be threadably coupled to the inner sheath such that axial rotation of the outer sheath relative to the inner sheath causes the outer sheath to move between the first and second positions. Alternatively, the outer sheath may be slidably coupled to the inner sheath. In any case, positioning the outer sheath in the first position causes compression of the distal end of the inner sheath, thereby creating a tapered lumen. Likewise, positioning the outer sheath in the second position enables the distal end of the inner sheath to expand sufficiently to allow the medical device to pass through the lumen In another embodiment of the present invention, a device shield include an expanded portion, a storage portion, and a rifled portion. The expanded portion directs a guide wire into a guide wire lumen of a medical device. The storage portion is adapted to have the medical device disposed therein. The rifled portion is adapted to create one or more folds in the medical device as the medical device is passed into or out of the storage portion through the rifled portion. In one embodiment, the rifled portion includes a generally cylindrical channel having one or more spiral grooves or ridges. In another embodiment, the rifled portion includes a generally cylindrical channel having one or more grooves or ridges that are axially aligned with the device shield. In still another embodiment, the rifled portion includes a first portion and a second portion, the first portion having one or more spiral grooves or ridges, and the second portion having one or more grooves or ridges that are axially aligned with the guide wire loading device.

Additional features and advantages of the disclosure will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify at least some of the advantages and features of the present disclosure, a more particular description will be rendered by reference to specific embodiments thereof, which are illustrated in the appended drawings. It is appreciated that these drawings depict only illustrated embodiments and are therefore not to be considered limiting of its scope. The disclosure will be described and explained with additional specificity and detail through the use of the accompanying drawings in which:

FIG. 3 illustrates an embodiment of a device shield for a medical device;

FIG. 4 illustrates an embodiment of a device shield in use;

DETAILED DESCRIPTION

I. Introduction

The present disclosure is related to device shields for packaging and protecting medical devices (e.g., balloon expandable, self-expanding, or other stents; luminal filters; or other implantable devices, or other medical devices) and/or at least a portion of a delivery device (e.g. balloon catheters, self-deploying stent catheters, vena cava filter delivery catheters, or other delivery devices) during storage and deployment. Stent retention, surface integrity, and crossing profile are exemplary characteristics of a stent or other medical device that may be important to positive clinical outcomes. At least one of these characteristics may be positively impacted by at least one embodiment of a device shield described herein. For example, a device shield may constrain the dimensions of the stent and/or balloon during the storage process, which may impact the overall profile and/or stent retention by limiting expansion during storage. It may be possible for a stent and/or balloon to expand slightly during storage due to residual stresses and/or fluctuations in humidity and/or temperature. Even slight expansions of the stent may negatively affect stent retention and/or crossing profile.

Furthermore, a device shield may limit the adhesion of free particulates in the surrounding environment or on a surgeon's gloves from contacting the medical device and/or a portion of the delivery device. Without a device shield, a guide wire or other device may scratch the medical device and/or delivery device. Additionally, contaminants may deposit on the medical device and/or delivery device. Either of these events may adversely impact product performance and/or clinical outcome.

Figure 1A:
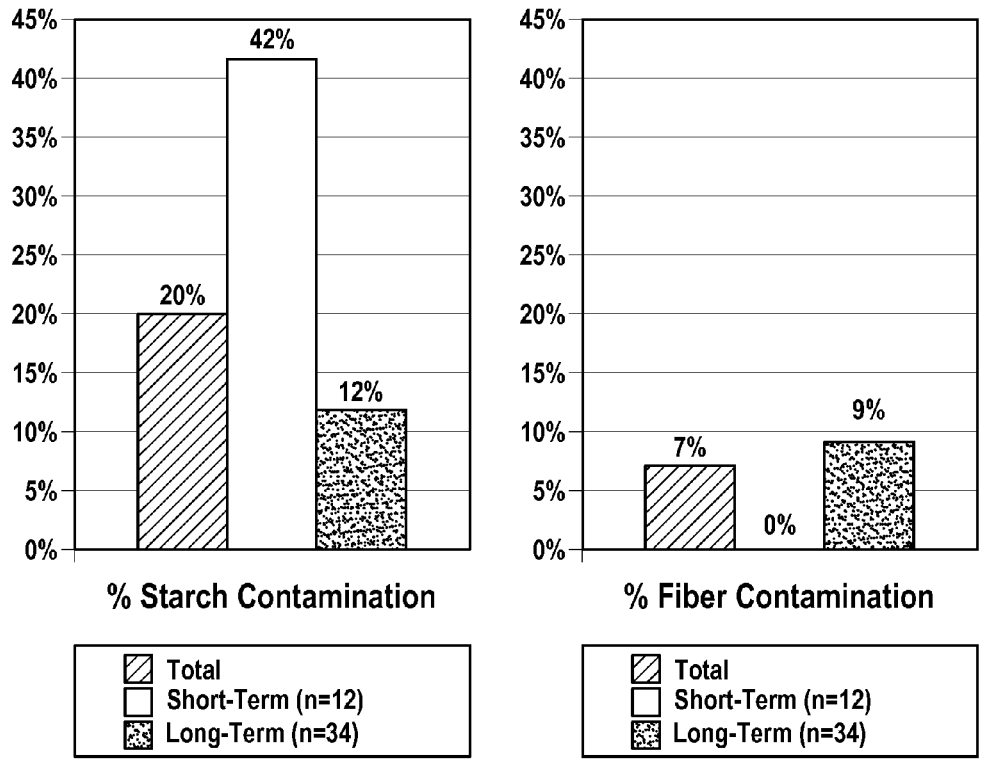
FIG. 1A illustrates an analysis of contaminants found on implanted stents.
Figure 1B:
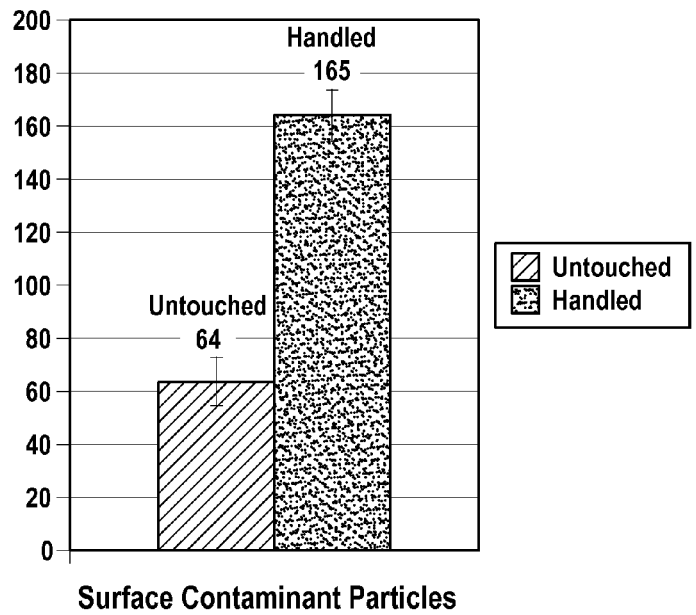
FIG. 1B illustrates a comparison of contaminants found on handled and untouched stents.
Figure 1C:
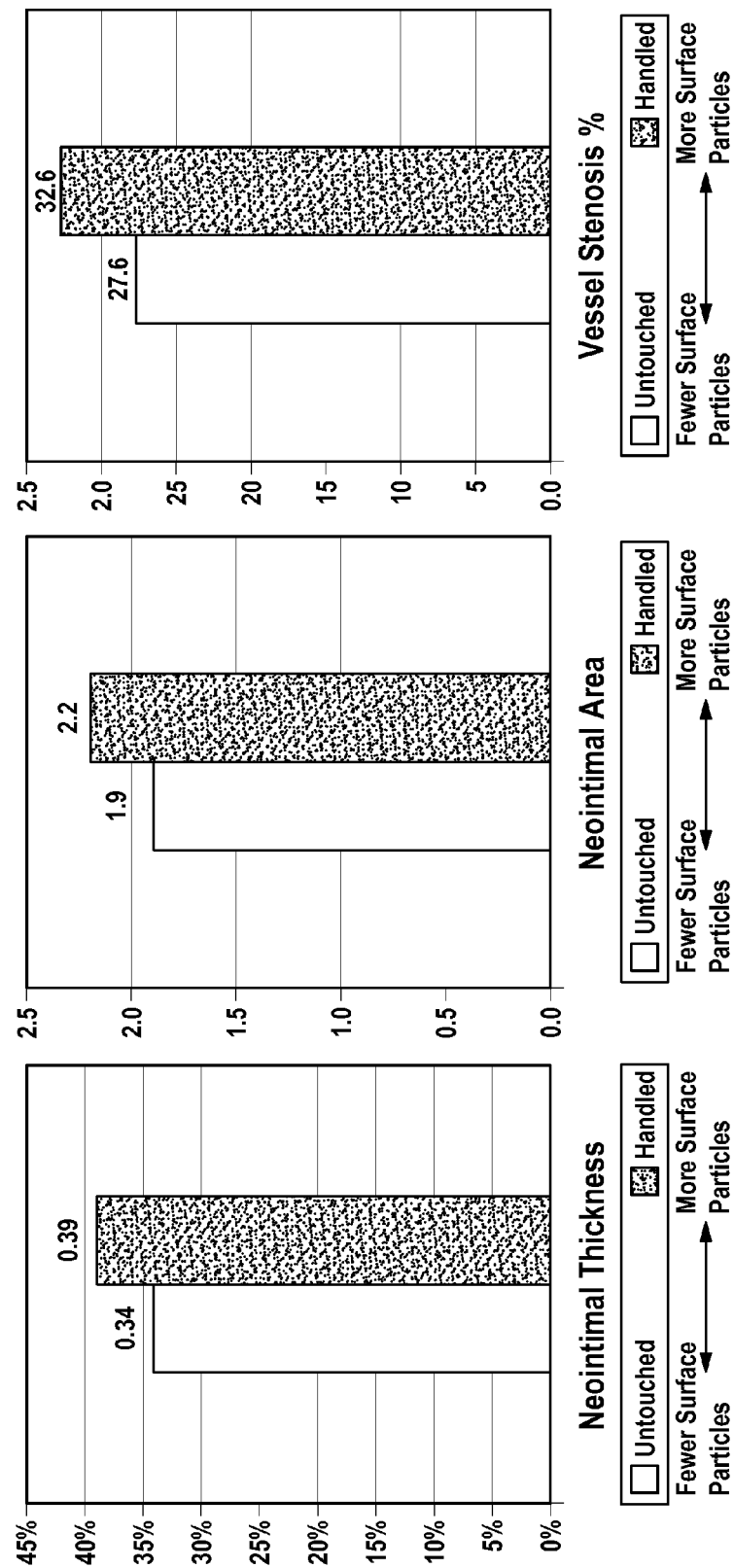
FIG. 1C illustrates the clinical outcomes of stents that are untouched and stents that have been handled.

Referring now to FIGS. 1A-1C, data are presented showing that many medical devices (in this case stents) show high levels of contaminants and that reduced contamination tends to lead to more favorable clinical outcomes. FIG. 1A presents results from an analysis of porcine implanted stents in pre-clinical studies showing a high level of contaminants. The animals were classified into two groups based on the length of follow-up (i.e., "short-term" and "long-term"). The data indicates that high percentages of stents in both short-term and long-term groups have high percentages of starch contamination and fiber contamination. Typical routes of contamination include, but are not limited to, handling the stents, dust particles in the air landing on the stents prior to implantation, or other contamination routes. For example, while most cardiologists use so-called "powder-free" gloves, some still use powdered gloves, which may increase the level of contaminants on the stent. Furthermore, even powder-free gloves may not be contaminant free.

FIG. 1B presents results from an analysis of the numbers of surface contaminants on handled and untouched stents. In this study, handled stents had approximately 165 surface contaminant particles per stent. In contrast, untouched stents had only an average of 64 surface contaminant particles per stent.

FIG. 1C presents results comparing various clinical outcome markers for untouched, and handled stents. In general, the results indicate that cleaner stents have better clinical outcomes. For example, cleaner stents (i.e., untouched) show better neointimal thickness, neointimal area, and lower vessel stenosis when compared to stents that have been handled.

Further discussion of the data and study can be found in Catheterization and Cardiovascular Diagnosis 40:238-332 (1997). D. M. Whelan, BSc, H. M. M. van Beusekom, PhD, and W. J. van der Giessen, MD, PhD. "Foreign Body Contamination During Stent Implantation," the entirety of which is incorporated herein by reference.

While the data from FIGS. 1A-1C show that protecting an implantable medical device from contamination may result in improved clinical outcomes, the devices and methods of the present invention may provide even better or more improved clinical outcomes than those in FIGS. 1A-1C. This is because embodiments of the present invention provide more protection to the implantable device prior to insertion into an access device. According to the procedures used to obtain the data in FIGS. 1A-1C, the implantable device was uncovered prior to insertion into an access device, such as an RHV. With the implantable device being uncovered, the implantable device may have been exposed to particulates, other contaminates, or a higher likelihood of damage. Although the devices used in connection with FIGS. 1A-1C shielded the implantable device from contamination for a while, the devices were removed prior to insertion of the implantable devices into an access device. During the time between uncovering the implantable devices and insertion into an access device, the implantable devices were exposed to contamination and damage. Thus, although the devices used in connection with FIGS. 1A-1C may have limited the contamination of the implantable devices, which would likely lead to improved clinical outcomes, the exposure to contamination between removal of the shielding devices and insertion into the access devices would limit how much the clinical outcomes could be improved.

In contrast, according to some embodiments of the present invention, the implantable devices are not uncovered or exposed prior to insertion into an access device. As a result, the implantable devices are shielded from contamination or damage from the time the packaging is opened, through the loading of the guide wire, and until the implantable device is inserted into the access device. Thus, according to some embodiments of the present invention, the implantable devices remains covered and protected from contamination and damage until the implantable device is inserted into the access device, which may provide even further improved clinical outcomes than those described shown in FIGS. 1A-1C.

Figure 2:
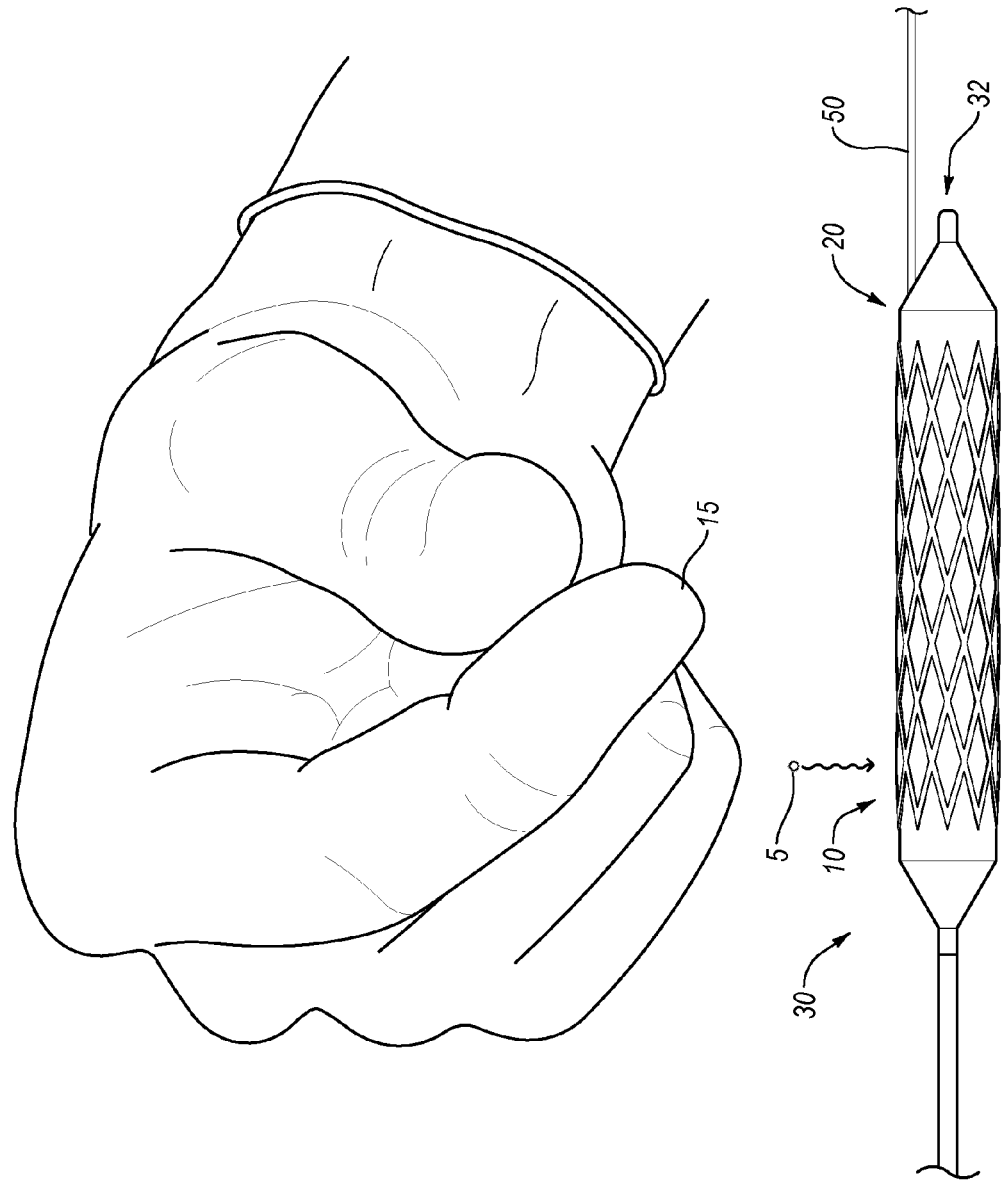
FIG. 2 illustrates a typical stent loaded onto a balloon and illustrates examples of how stents can be damaged or become contaminated.

FIG. 2 illustrates a typical balloon expandable stent 10 loaded onto a balloon 20. FIG. 2 also illustrates several examples of ways a medical device, such as stent 10 and/or a balloon 20, can be damaged during the process of deploying the medical device into a patient's body. For example, FIG. 2 illustrates an attempted insertion of a guide wire 50 into a stent delivery device 30. If the guide wire 50 misses the guide wire lumen 32 of the stent delivery device 30, the guide wire 50 may scratch or otherwise damage the stent 10 and/or balloon 20. In addition, particulates (e.g., particulate 5) or hand 15 may contact the medical device (e.g. the stent 10) and/or the delivery device (e.g. balloon 20) potentially contaminating the stent 10 and/or balloon 20. For example, the particulate 5 may be inserted into a patient anatomy with the stent 10 and/or balloon 20.

The data illustrated in FIGS. 1A-1C and the schematic presentation as shown in FIG. 2 suggest the need for devices and methods for preventing contamination of medical devices and/or delivery devices prior to insertion into a patient's body in order to reduce the risk of surface contamination and to improve clinical outcomes. As such, there is a need for at least one of the following: easier guide wire insertion into a catheter lumen, minimizing surface interruption or damage of the medical device and/or delivery device before and/or during guide wire loading, maintaining the medical device and/or delivery device in a pre-deployed configuration minimizing contamination of the medical device and/or delivery device surfaces before insertion into a patient, facilitating insertion into an access device, such as an RHV, simplifying removal of the loading tool, restraining the loading tool from insertion into a patient's anatomy, insertion without a need for removal of the sheath in a separate step, or combinations thereof. At least one embodiment of the present disclosure may fulfill at least one of these needs. FIGS. 1A-1C also indicate that vascular response and/or clinical outcome is related to cleanliness of the medical device. Although an operating room is typically clean, a risk of contamination may exist because of handling of a stent with a sterile gloved hand and/or particulates in the environment may deposit on a medical device prior to insertion into the patient anatomy.

II. Device Shields

FIG. 3 illustrates an embodiment of a device shield 100 that can be used to package and protect a medical device and/or a portion of a delivery device during storage and delivery to a patient's body. The device shield 100 may include a generally cylindrical body and/or generally cylindrical inner surface (not shown). The stent (shown as 10 in FIG. 2), the balloon (shown as 20 in FIG. 2), and a distal portion of the stent delivery device 30 may be at least partially stored within a storage portion 104 of the device shield 100.

The device shield 100 may include an expanded portion 102. The expanded portion 102 may be fluted and/or flared to receive a guide wire 50. The expanded portion 102 may further guide the guide wire 50 into a guide wire lumen (shown as 32 in FIG. 2) and prevent damage to the stent and/or balloon (shown as 10 and 20, respectively in FIG. 2) if the guide wire 50 misses the insertion point for the guide wire lumen. The expanded portion 102 may facilitate insertion of a guide wire 50 into the guide wire lumen 32 while reducing the risk of the guide wire 50 scratching, puncturing, and/or otherwise contacting or damaging the balloon and/or stent components. The device shield 100 may also protect the stent and/or balloon (shown as 10 and 20, respectively in FIG. 2) surfaces prior to and/or during insertion into the patient anatomy by allowing the stent and balloon to be delivered into the patient's body without having to unpackage the balloon and stent component and without having to hold the stent to load the guide wire or load the stent into an access device.

In some embodiments, the device shield 100 may include a limit element 106 that may prevent the stent and/or balloon (shown as 10 and 20, respectively in FIG. 2) from moving out of the device shield 100. For example, the limit element tabs shown as 106 may be connected to projections or the like that extend into the interior lumen of the device shield 100 and prevent movement of the stent and/or balloon relative to the device shield 100. The limit element 106 may also prevent the device shield 100 from being inserted beyond a predetermined distance into the patient anatomy. Limit element 106 may be flexible. In the present embodiment, limit element 106 may include protrusions 108 that extend laterally and/or in a distal direction. These protrusions 108 may increase the profile of the device shield 100, thereby restricting the device shield 100 from being inserted too far into a rotating hemostatic valve (RHV), catheter end, or other access to the patient anatomy. For example, the protrusions 108 may have a larger cross-sectional profile relative to a longitudinal axis of the device shield 100 compared to a cross-sectional profile of the device shield 100 at a distal-most end of the expanded portion 102, making the cross-sectional profile of the protrusions 108 the largest cross-sectional profile of the device shield relative to the longitudinal axis.

FIG. 4 illustrates an embodiment of the limit element 106 in use. In this embodiment, the device shield 100 and the stent delivery device 30 may be inserted into a RHV 290. As shown in FIG. 4, the guide wire 50 may be inserted through the expanded portion 102 and the storage portion 104 and exit the proximal end of the device shield 100. The device shield 100 may be inserted into the RHV 290. To prevent over-insertion of the device shield 100, the limit element 106 may engage the proximal end of the RHV 290.

Thus, the expanded portion 102 of the device shield 100 may be inserted at least partially into the RHV 290 as shown in FIG. 4, but its progress may be restricted by the limit element 106. As the stent and balloon are stored within the storage portion 104, the stent and balloon may remain stored until they are at least partially inserted into the RHV 290 or other access device. This may significantly reduce the risk of damage and/or contamination by free particulates.

Figure 5:
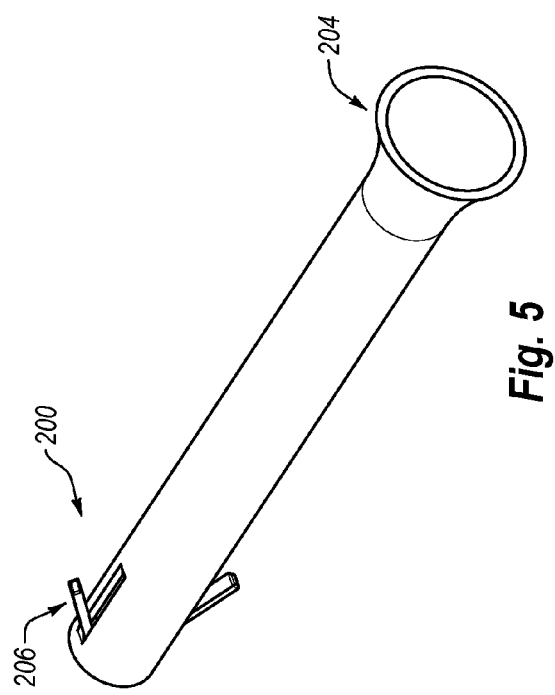
FIG. 5 illustrates another embodiment of a device shield guide for a medical device.

As shown in FIG. 5, some embodiments of the device shield having a limit element, such as device shield 200 and limit element 206, may be integrally formed. For example, limit element 206 may be cut into an outer surface (not shown) of the device shield 200. The limit element 206 may then be deformed from an undeformed state to a deformed state. For example, the limit element 206 may be deformed away from a longitudinal axis (not shown) of the device shield 200. The limit element 206 may be restricted from returning to the undeformed state. For example, the limit element 206 may be strained past its yield limit as it is deformed to the deformed state, may be heat set while in the deformed state, may be otherwise restricted, or combinations thereof. Although the device shields 100, 200 shown in FIGS. 3-5 are shown with two limit elements 106, 206, more and/or fewer limit elements may be used.

Figure 6:
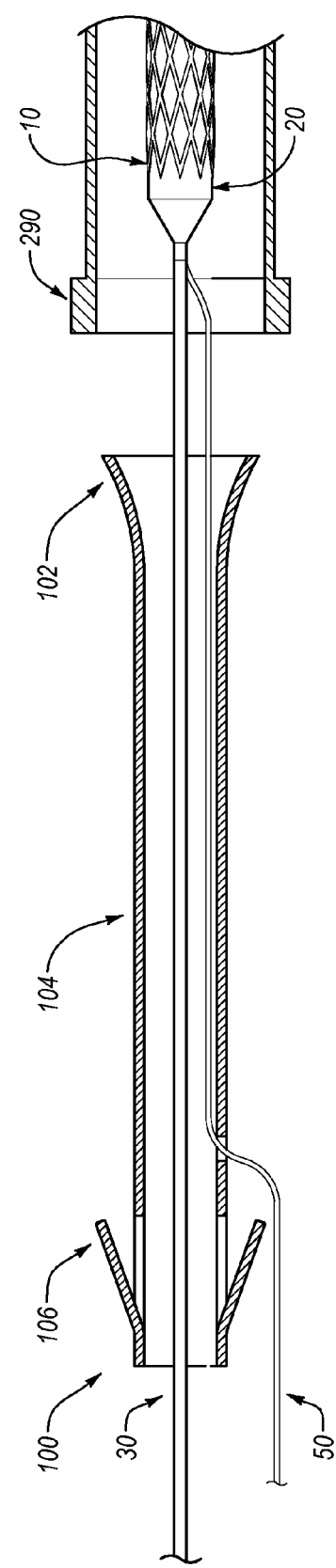
FIG. 6 illustrates delivery of a stent and a balloon catheter into an access device using an embodiment of a device shield.

As shown in FIG. 6, after insertion of the stent 10 and/or balloon 20 into an access device, such as RHV 290, the device shield 100 may be removed proximally before, during, and/or after the stent delivery device 30 is inserted into the access device. For example, the stent delivery device 30 may be urged distally into the access device as the device shield 100 is urged proximally.

Figure 7A:
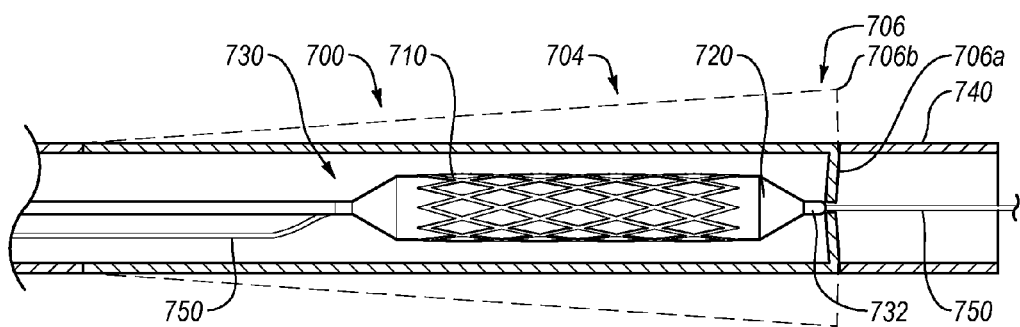
FIG. 7A illustrates an embodiment of a device shield for a medical device having a gate-type limit element.
Figure 7B:
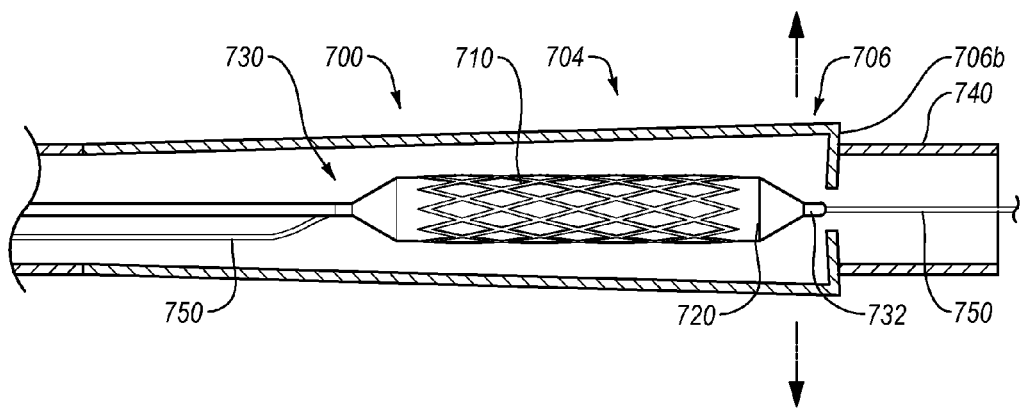
FIG. 7B illustrates the device shield of FIG. 7A with the limit element in a partially opened configuration.
Figure 7C:
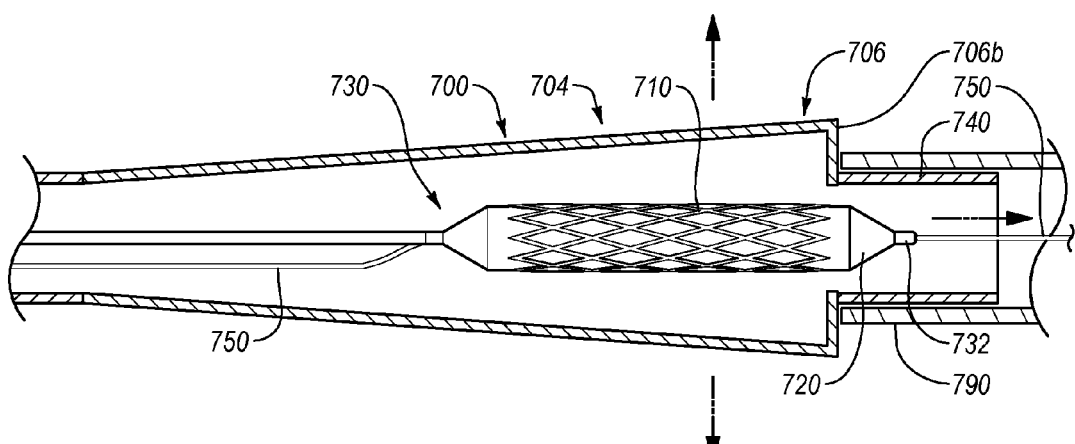
FIG. 7C illustrates the device shield of FIG. 7A with the limit element in a fully opened configuration and with the stent stored in the device shield being deployed into an access device.

Referring now to FIGS. 7A-7C, partial cut-away views of another embodiment of a device shield 700 are illustrated.

The device shield 700 includes a housing 704 that is used to maintain or package a medical device 710 (e.g., a stent), a balloon 720 associated with the medical device 710 and at least a portion of a medical device delivery apparatus 730 until the stent is to be implanted in a patient's body. The device shield 700 includes a gate-type limit element 706 that can be transitioned from a closed position 706a to an opened position 706b.

In the closed position 706a illustrated in FIG. 7A, the limit element 706 prevents the stent 710 and balloon 720 from being pushed out of the device shield 700. The limit element 706 also serves to prevent contaminants from depositing on the stent 710 or the balloon 720 while the stent 710 or the balloon 720 device are in storage. For example, the limit element 706 may substantially enclose the stent 710 and the balloon 720 to prevent and/or reduce damage or outside contamination. Optionally, as shown on the illustrated embodiment, a small gap can be left in the limit element 706 and the distal end of the stent delivery device 730 can be inserted into the gap such that a guide wire 750 can be safely guided into the guide wire lumen 732 of the stent delivery device 730.

FIGS. 7B and 7C illustrate the transitioning of the limit element 706 from the closed state 706a to an opened state 706b. In addition, in FIG. 7C, an outlet tube 740 of the device shield 700 is inserted into an access device 790 (e.g., an RHV) such that the stent 710 and balloon 720 can be deployed from the device shield into a patient's body. As with previously described embodiments, the limit element 706 in the opened position 706b may prevent over-insertion of the device shield 700 into the access device 790 by the opened limit element 706b engaging with the proximal end of the access device 790.

The limit element 706 may include multiple components. For example, as shown in FIGS. 7A-7C, the limit element 706 is shown with upper and lower components that may each independently transition from the closed state 706a to the open state 706b. In other embodiments, the limit element 706 may include a component that does not move and a component that does move. For example, the stationary component may only partially extend into a central portion of the device shield 700 while the moveable component may extend across the central portion to provide the function of transitioning from a closed to an open state. In other words, the moveable component may abut or overlap the stationary component. Other combinations are also contemplated. For example, the upper and lower components of the limit element 706 shown in FIGS. 7A-7C may overlap or otherwise interact to minimize exposure of the medical device to environmental particulates and/or damage.

Referring now to FIGS. 8A-8F, another embodiment of a device shield 800 is illustrated. Device shield 800 has a split design, allowing the device shield 800 to be a unified body during assembly, storage, guide wire loading, and deployment of a stent and a catheter and to be split open after catheter advancement into the patient anatomy. This design allows for optimal protection of the medical device distal end during shipment, unpackaging, and system advancement, but also allows for a compact form factor and intuitive operation.

Figure 8A:
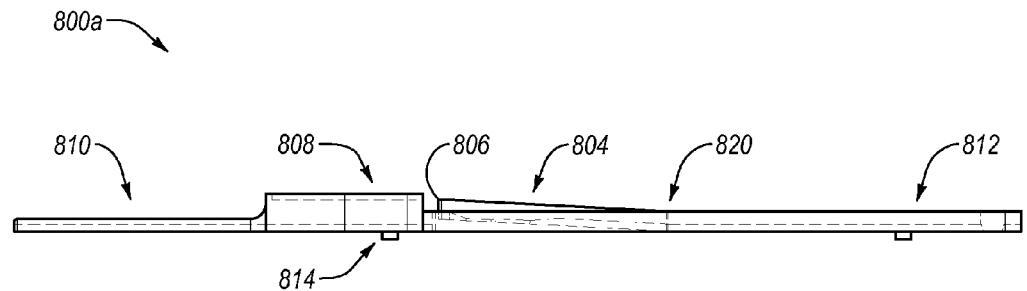
FIG. 8A illustrates a side view of a first half of a device shield according to one embodiment of the invention.
Figure 8B:
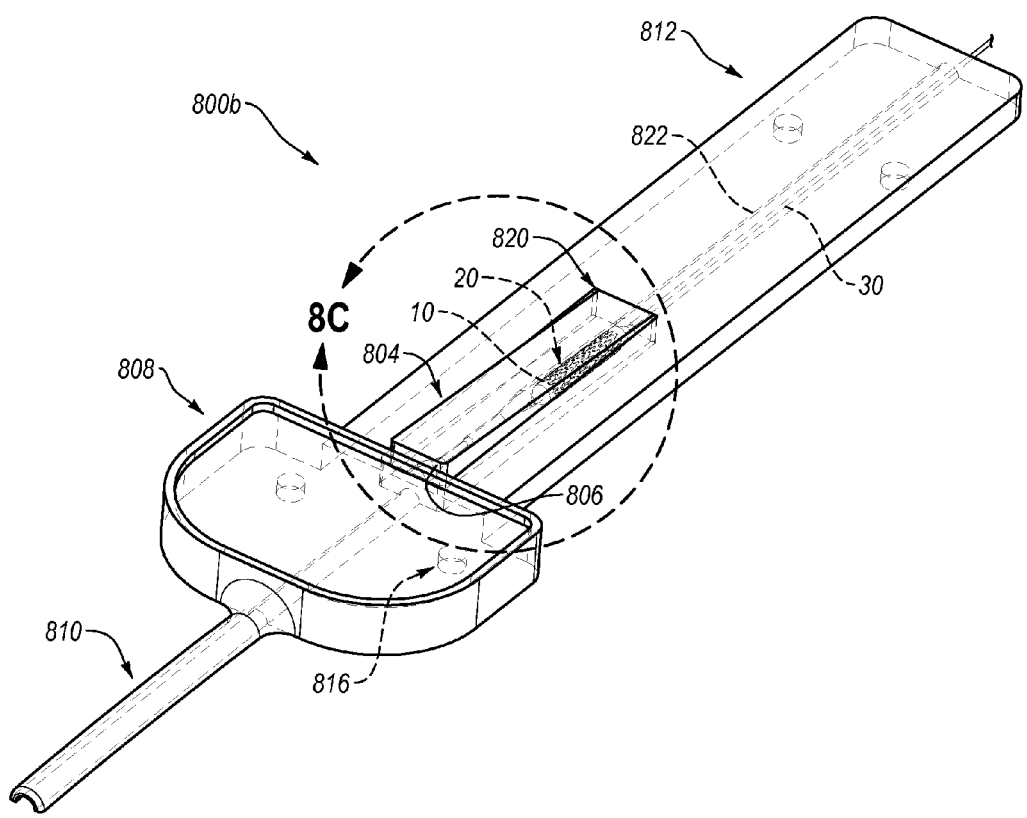
FIG. 8B illustrates an isometric view of a second half of the device shield illustrated in FIG. 8A.

Referring to FIGS. 8A and 8B, a side view of a first half 800a of the device shield 800 is illustrated in FIG. 8A and an isometric view of a second half 800b of the device shield 800 is illustrated in FIG. 8B. In the present embodiment, the first half 800a and the second half 800b are similar in most respects, although the first half 800a includes at least one orientation protrusion 814 and the second half 800b includes at least one orientation aperture 816. Other orientation features may be used. In other embodiments, the first half 800a and the second half 800b may differ. For example, only one of the first half 800a and the second half 800b may include a storage portion 804. In further embodiments, the device shield 800 may be formed as a generally unitary body. For example, the majority of the device shield 800 may be integrally formed using, for example, injection molding.

The first half 800a and second half 800b may be joined during assembly, storage, guide wire loading, and deployment of a stent and/or may be split open after advancement of the catheter into the patient anatomy. The first half 800a and second half 800b of the device shield 800 each include a body portion 812, a storage portion 804 formed in the body portion 812 that is configured to store and protect a medical device and a medical device delivery apparatus during storage and delivery, and a limit element 806 configured to constrain the medical device and the medical device delivery apparatus. For example, the limit element 806 may prevent distal longitudinal translation toward an insertion stem 810. The first half 800a and second half 800b of the device shield 800 further include a hinged portion 820 that facilitates transition of the limit element 806 from a constraining position to a releasing position. The hinged portion 820 may include a living hinge or other hinge mechanism. The first half 800a and second half 800b of the device shield 800 may include an expanded portion 808 at the distal end of the body portion 812. In other embodiments, storage portion 804 and the limit element 806 may be flexible.

The insertion stem 810 includes an interior lumen 818 that can be used to insert a stent delivery system, a catheter device, or other medical devices through the device shield 800 into an access device. The insertion stem 810 may be used to insert the device shield 800 into an access device, such as RHV 290 described above. The expanded portion 808 may be used as a grip to facilitate insertion and/or maintain the position of the stem 810 within the access device.

Figure 8C:
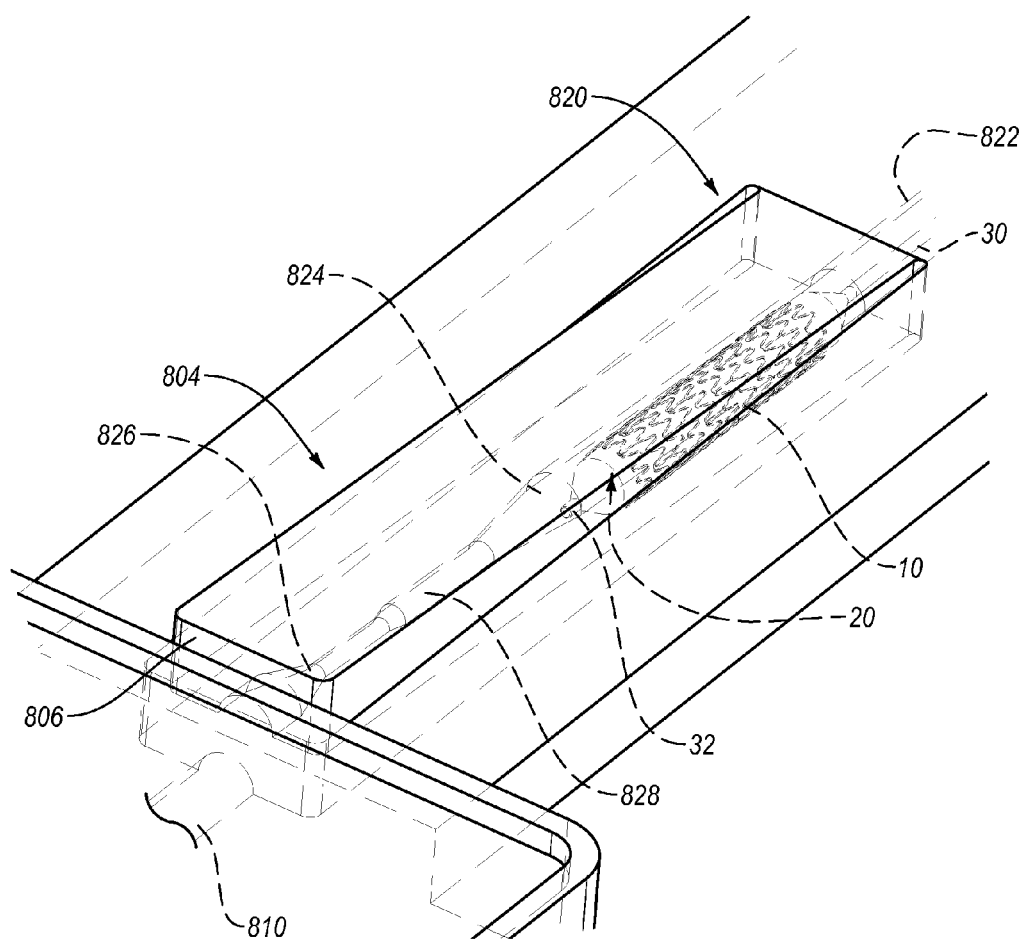
FIG. 8C illustrates a close-up view of a medical device storage portion of the device shield depicted in FIG. 8B.

FIG. 8B illustrates a stent 10, a balloon 20, and a delivery catheter 30 disposed in the body 812 and the storage portion 804. FIG. 8C illustrates an enlarged view of the storage portion 804 and the stent 10 and the balloon 20. The body 812 includes a lumen 822 configured to allow the delivery catheter 30 to pass through the body 812. As can be seen more clearly in FIG. 8C, the storage portion 804 includes a molded portion 824 that is shaped to conform to the shape of the stent 10 and the balloon 20. In other embodiments, the molded portion 824 can be shaped to conform to the shapes of other types of medical devices. The molded portion may also be configured to restrain movement of the stent 10 and balloon 20 when the limit element 806 is in a down position (see, e.g., 706a in FIG. 7A). For example, longitudinal movement of the stent 10 and/or balloon 20 may be restrained. The molded portion 824 may also be configured to constrain the dimensions of the stent 10 and the balloon 20 to prevent dimensional changes to either the stent 10 or the balloon 20 during storage. For example, a radial and/or longitudinal dimension of the stent 10 and/or balloon 20 may be constrained. Although the storage portion 804 is described in connection with the balloon 20 of a balloon catheter and a balloon-expandable stent 10, the storage portion may be used with other medical devices and/or delivery devices.

As can be further seen in FIG. 8C, in the present embodiment, the molded portion 824 includes an expanded portion 826 that feeds into a passageway 828 to facilitate insertion of a guide wire into guide wire lumen 32 of the insertion catheter 30. In practice, a guide wire can be fed through insertion stem 810, through the expanded portion 826, and into guide wire lumen 32 without risk of damaging the stent 10 or the balloon 20. In other embodiments, the molded portion 824 may omit the expanded portion 826.

In one embodiment, the first half 800a and/or second half 800b may be at least partially formed of clear plastic, which may facilitate verification of contents within the device shield 800. In some embodiments, a lens may be formed into the device shield 800 in order to facilitate visual inspection of the contents of the device shield 800.

In the present embodiment, the storage portion 804 and the limit element 806 are shown deflected outward. This deflection may be accomplished by biasing the limit element 806 toward an outward position. For example, a living hinge may be formed in such a way to accomplish this bias, a biasing element, such as a spring, may be used, or other features or processes may be utilized to outwardly bias the limit element 806. The storage portion 804 and the limit element 806 may be deflected inward when a constraining device such as a retaining member 850 is placed over the body 812, the storage portion 804, and the limit element 806, as will be explained further herein below.

In some embodiments, the device shield 800 and storage portion 804 may be integrally formed. For example, storage portion 804 may be formed into an outer surface (not shown) of the device shield 800. The storage portion 804 may then be deformed from an undeformed state to a deformed state. For example, the storage portion 804 may be deformed away from a longitudinal axis (not shown) of the device shield 800. The storage portion 804 may be restricted from returning to the undeformed state. For example, the storage portion 804 may be strained past its yield limit as it is deformed to the deformed state, may be heat set while in the deformed state, may be otherwise restricted, or combinations thereof. In the present embodiment, the hinge 820 may be a flexible hinge.

Figure 8D:
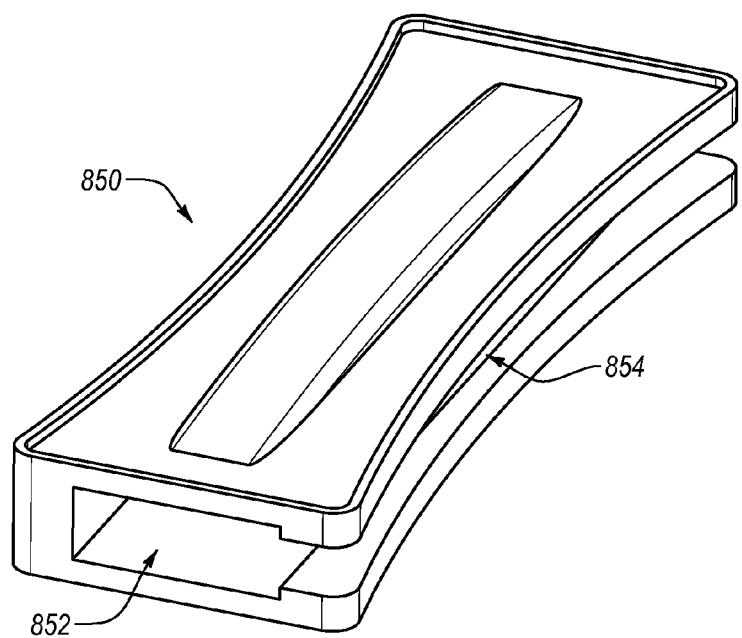
FIG. 8D illustrates a retaining member configured to be disposed around the device shield of FIGS. 8A and 8B.
Figure 8E:
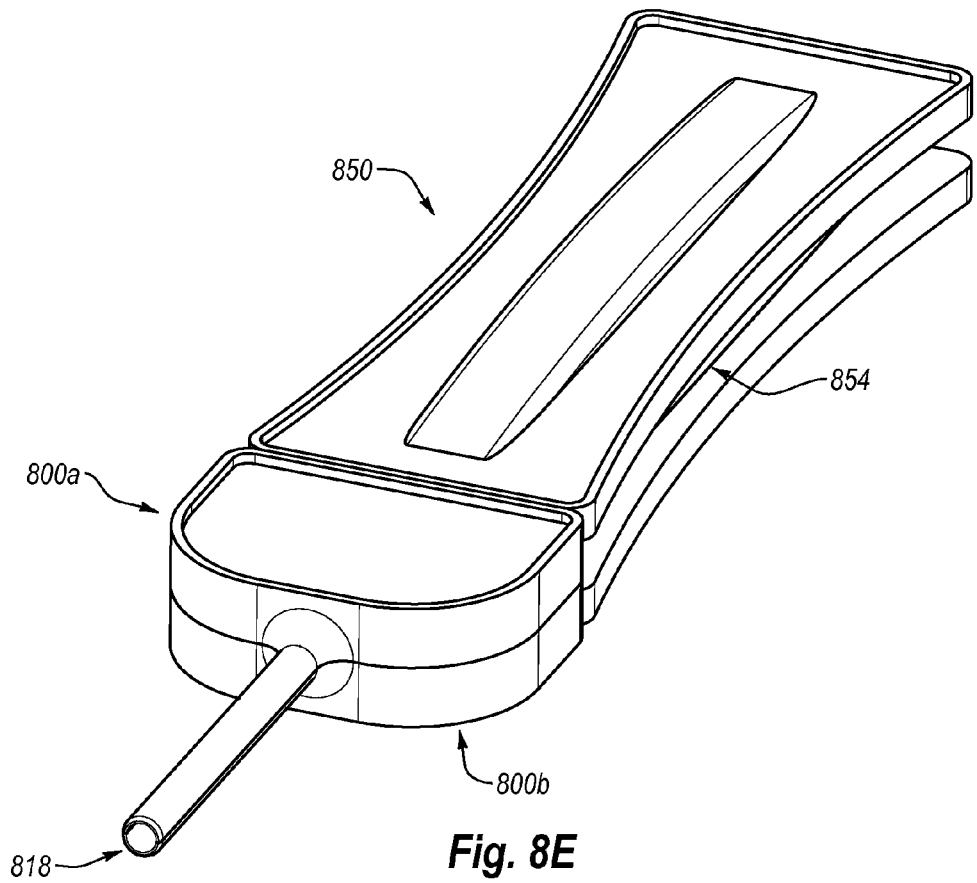
FIG. 8E illustrates the device shield having the retaining member of FIG. 8D disposed therearound.
Figure 8F:
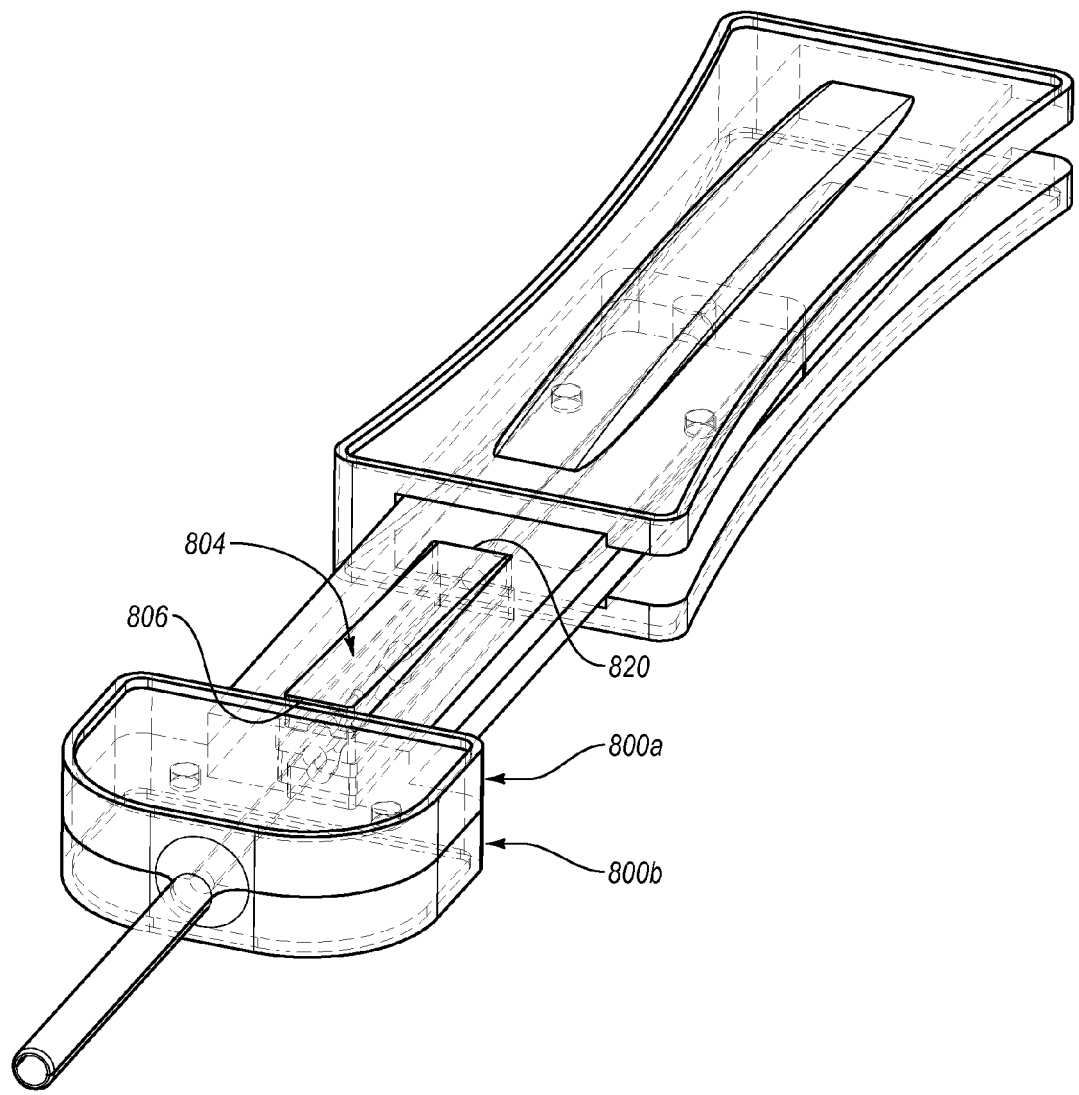
FIG. 8F illustrates the device shield of FIG. 8E with the retaining member in a retracted position.

Referring now to FIGS. 8D-8F, an embodiment of a retaining member 850 is illustrated. The retaining member 850 may be disposed around the device shield 800, as shown in FIG. 8E. When the retaining member 850 is disposed around the device shield 800, at least one of the storage portions 804 and the limit elements 806 may be deflected toward the longitudinal axis of the device 800, i.e., in a restraining state. At least one of the storage portions 804 and/or the limit elements 806 may limit movement, expansion, and/or other changes to the stent and/or balloon while in the restraining state.

In some embodiments, the retaining member 850 may include a device receiving aperture 852. The device shield 800 may be inserted into the device receiving aperture 852. In the present embodiment, the retaining member 850 may include a lateral aperture 854. In some embodiments, the lateral aperture 854 may provide access to the device shield 800 during use.

As the device shield 800 is inserted through the device receiving aperture 852, at least one of the storage portions 804 and/or the limit elements 806 may be deflected towards the longitudinal axis of the device 800, i.e., into the constraining state. With at least one storage portion 804 and/or the limit element 806 in the constraining state, the stent delivery catheter may be generally restrained within the device shield.

In this constraining state, as shown in FIG. 8E, device shield 800 may entirely constrain and/or protect a distal portion of the medical device, i.e., a stent delivery device 30. With the medical device generally constrained, a guide wire, such as guide wire 50, may be inserted into the insertion stem 810, the passageway or lumen 818, and the guide wire lumen, such as guide wire lumen 32, of the stent delivery device 30. The guide wire may follow the lumen and/or may be guided into the guide wire lumen of the stent delivery device through the expanded portion 826 that may be, for example, formed in at least one of the limit elements 806.

Constraining the stent and/or balloon may be beneficial because the physician may not have to strain his eyesight to find a relatively small guide wire lumen of the stent delivery device but need only insert the guide wire into the relatively large lumen 818 of the insertion stem 810 and advance it smoothly.

Once the guide wire is associated with the device shield, i.e., the guide wire has exited a proximal end of the device shield, the insertion stem 810 may be inserted into an access device, such as an open RHV.

Referring now to FIG. 8F, once the insertion stem 810 is inserted into the access device, the retaining member 850 may be at least partially retracted to allow at least one of the limit elements 806 to deflect toward an open state. Once the limit elements 806 are allowed to move outward to an open state, the previously constrained medical device, i.e., stent delivery device 30, may be advanced through the insertion stem 810 over the guide wire. Prior to movement of the limit elements 806 toward the open state, the constrained medical device would have been unable to advance through the insertion stem 810 due to the closed state of the limit elements 806.

Once the distal portion of the medical device is fully within the access device, the entire device shield 800 may be retracted over the stent deployment device. The retaining member 850 may be fully removed from device shield 800. In split device shield embodiments, first half 800a and second half 800b may be separated by pulling them apart or simply allowing one portion to fall away from the other. The physician is left with the stent delivery device advanced into the patient.

Figure 9A:
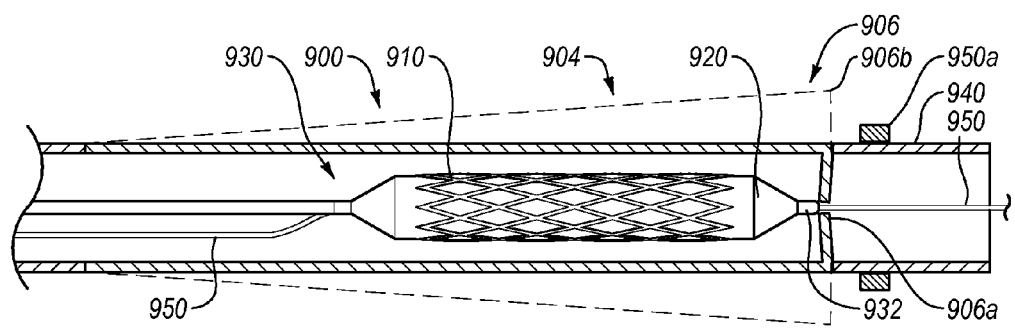
FIG. 9A illustrates yet another embodiment of a device shield for a medical device having an actuator for opening a gate-type limit element.
Figure 9B:
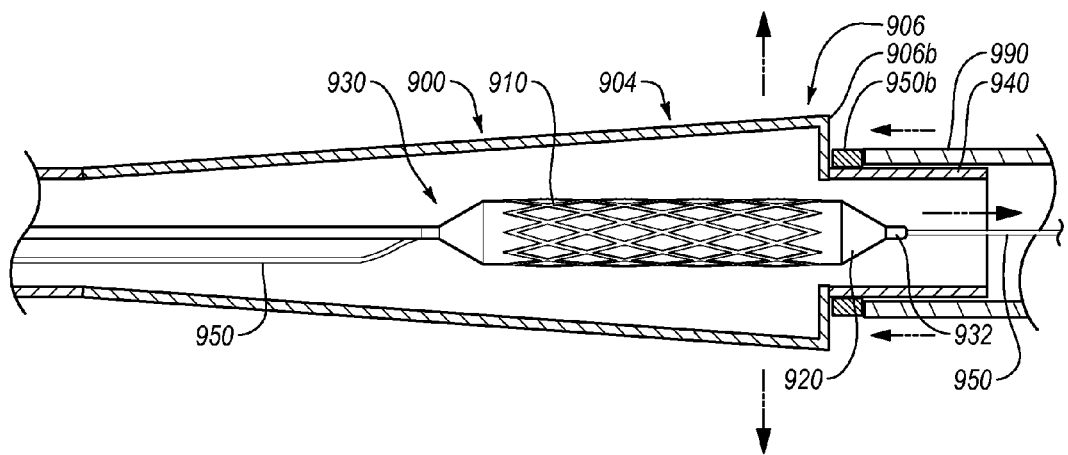
FIG. 9B illustrates the device shield of FIG. 9A with the limit element in a fully opened configuration and with the stent stored in the device shield being deployed into an access device.

Referring now to FIGS. 9A and 9B, a partial cut-away view of an alternative embodiment of a device shield 900 is illustrated. The device shield includes an actuator 950a-b that can be used to automatically transition a limit element 906 from a closed position 906a to an opened position 906b when the device 900 is inserted into an access device 990. The device shield 900 includes a housing 904 that is used to maintain or package a medical device 910 (e.g., a stent), a balloon 920 associated with the medical device 910 and at least a portion of a medical device delivery apparatus 930 until the stent 910 is to be implanted in a patient's body.

In the closed position 906a illustrated in FIG. 9A, the limit element 906 prevents the stent 910 and balloon 920 from being pushed out of the device shield 900. The limit element 906 also serves to prevent contaminants from depositing on the stent 910 or the balloon 920 while the stent 910 or the balloon 920 device are in storage. Optionally, as shown on the illustrated embodiment, a small gap can be left in the limit element 906 and the distal end of the stent delivery device 930 can be inserted into the gap such that a guide wire 950 can be safely guided into the guide wire lumen 932 of the stent delivery device 930. In another embodiment, the limit element 906 may transition between a fully closed position, a partially open position, and a fully open position, where the stent 910 and balloon 920 are prevented from being pushed out of the device shield 900 in the fully closed and partially open position, the guide wire 950 may be inserted into the stent delivery device 930 in the partially open position, and the stent 910 and balloon 920 may be advanced in the fully open position.

FIG. 9B illustrates the transitioning of the limit element 906 from the closed state 906a to an opened state 906b. When the outlet tube 940 is inserted into an access device 990 (e.g., an RHV), the insertion motion causes the actuator 950a-b to be pushed back to position 950b, which opens the limit elements 906 to the opened position 906b. When the limit elements 906 are opened, the stent 910 and balloon 920 can be deployed from the device shield 900 into a patient's body. As with previously described embodiments, the limit element 906 in the opened position 906b may prevent over-insertion of the device shield 900 into the access device 990 by the opened limit element 906b engaging with the proximal end of the access device 990. In another embodiment, the actuator 950a-b may transition the limit element 906 between a fully closed position, a partially open position, and a fully open position.

Figure 10:
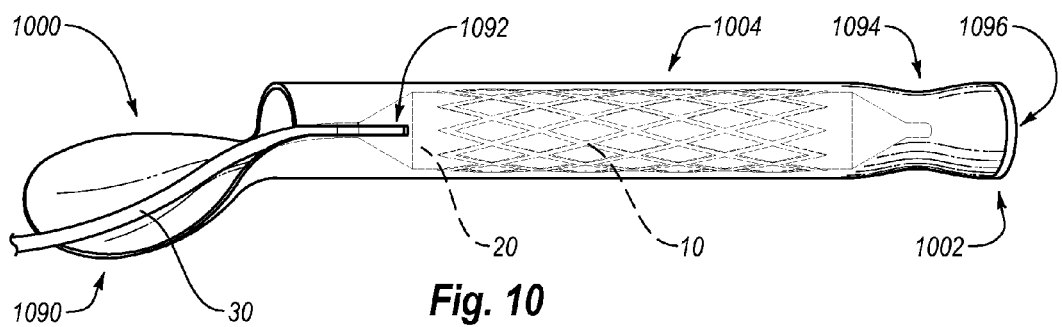
FIG. 10 illustrates a still further embodiment of a device shield for a medical device.

Referring now to FIG. 10, a still further embodiment of a device shield 1000 is illustrated. The device shield 1000 may incorporate other features from the other device shields described herein. For example, the device shield 1000 may include an expanded portion, such as expanded portions 102, 202, 1002, a limit element, such as limit elements 106, 206, 706, other elements, or combinations thereof. The device shield 1000 may include a storage portion 1004, which may include a generally cylindrical body and/or generally cylindrical inner surface (not shown) that may approximate the dimension of a crimped stent 10. For example, the inner diameter of the storage portion 1004 may be substantially similar to the diameter of the crimped stent 10, e.g. for a 0.040-inch crimped stent diameter the inner diameter of at least a part of the storage portion 1004 may be approximately 0.042-inch. The storage portion 1004 may have a length that can fully encompass the stent and/or balloon length during packaging and/or delivery.

The device shield 1000 may include an expanded portion 1002. The expanded portion 1002 may include a necked funnel 1094 that may facilitate insertion of the guide wire into a stent delivery device (shown as 30, in FIGS. 2-4). This expanded portion 1002 may be formed by heat shrinking the sheath material. In other embodiments, the necked portion 1094 may be swaged, crimped, or reduced in some other fashion that reduces one end of the expanded portion 1002 to form a funnel-like feature, or combinations thereof.

At least some embodiments may ease guide wire loading by, for example, positioning the distal end of the stent delivery device adjacent to the necked portion 1094 such that insertion of a guide wire into the stent delivery device may guide the guide wire. For example, the expanded portion 1002 may deflect the guide wire toward the center of the stent delivery device as it passes through the necked portion 1094 thereby inserting the guide wire into the distal end of the stent delivery device that may be located adjacent the necked portion 1094.

The distal end of the device shield 1000 may have a varied length. In some embodiments, it may have sufficient length for a physician to easily identify the opening and/or to facilitate guide wire insertion along the axial direction. For example, a length of approximately 10 mm beyond the necked portion 1094 may be sufficient in some instances.

In some embodiments, the expanded portion 1002 and/or the necked portion 1094 may be expandable or otherwise configured to facilitate insertion of the stent delivery device through the necked portion 1094 into an access device, such as an RHV. For example, the necked portion 1094 may include at least one expansion aperture 1096, such as a slit, channel, or other feature, to facilitate expansion of the expanded portion 1002 when a device, such as the stent delivery device, having a larger axial dimension is inserted through the necked portion 1094.

Expansion apertures 1096 may have various configurations. For example, at least one expansion aperture 1096 may be spiraled around the device shield 1000, the at least one expansion aperture 1096 may span the entire length of the expanded portion 1002, the at least one expansion aperture 1096 may be staggered along the length to facilitate use of multiple expansion apertures 1096 that do not span the entire length of the expanded portion 1002. The at least one expansion aperture 1096 may extend between a proximal end of the device shield 1000 and the distal end of the device shield 1000. In some embodiments, the at least one expansion aperture 1096 may extend between a proximal end of the expanded portion 1002 and a distal end of the expanded portion 1002. In further embodiments, the at least one expansion aperture 1096 may extend from a proximal end of the device shield 1000 and/or the expanded portion 1002 to a distal end of the device shield 1000 and/or the expanded portion 1002. In another example, the expanded portion 1002 may include an elastomeric portion.

Other configurations are contemplated to facilitate a lower profile, guide wire insertion, an expanded configuration that allows the stent delivery device to advance through the expanded portion 1002 without damaging the stent coating and/or causing the stent to be displaced on the stent delivery device, or other features.

In a further embodiment, the distal end of the device shield 1000 may include a colored tip that may provide greater visibility for a physician. The color may be provided by an ink, which may be bright colored, fluorescent, and/or glow-in-the-dark. A removable portion 1090 may be positioned near a proximal portion of the device shield 1000 that may facilitate removal of the device shield 1000 by the physician by grasping the removable portion 1090 while advancing the stent delivery device and/or proximally retracting the device shield 1000. In a further embodiment, a separation aperture 1092 may be provided that may create an opening in a side of the device shield 1000 to facilitate removal of the device shield 1000 from the stent delivery device.

A method of forming the expanded portion 1002 of the device shield 1000 may include inserting a tapered mandrel in one end that approximates the dimensions of the distal end of the stent delivery device. A second tapered mandrel, such as a hypotube, may be inserted through the device shield 1000 in an opposite direction such that the second mandrel extends over an end of the first mandrel. This overlap may facilitate the forming of a double-taper between the first and second mandrels and/or may vary the length of the expanded portion 1002 by moving the first and second mandrels relative to each other.

With the mandrels positioned within the device shield 1000 as described (e.g., inserted through opposing ends so the ends of the mandrels meet), the device shield 1000 can be further processed or undergo further process steps. Having the mandrels so positioned within the device shield 1000, the mandrels can maintain the desired shape of the device shield 1000, and the expanded portion 1002 in particular, as further processing takes place. For instance, with the mandrels so positioned within device shield 1000, the body of the device shield 1000 can undergo a heat shrink formation process to form expanded portion 1002. Likewise, in other embodiments, a necking operation can also be used to reduce the diameter of the body of the device shield 1000 to conform to the mandrel profile, thereby forming the expanded portion 1002. Furthermore, a combination of heating, heat shrinking, and/or necking can be used to form the tapered profile of the expanded portion 1002.

An exemplary method of using a guide wire loading tool, such as device shield 1000, may include positioning the device shield 1000 over a stent delivery device so that a distal end of the stent delivery device may be positioned adjacent the expanded portion 1002. The guide wire loading tool 1000 and stent delivery device may be removed from its packaging. A guide wire may be inserted into the device shield 1000 through its distal end until the guide wire is directed into and/or through a lumen of the stent delivery device. The guide wire loading tool 1000, with the stent delivery device, may be inserted into an access device, such as an RHV.

In embodiments with a removable portion 1090, the guide wire loading tool 1000, with the stent delivery device, may be inserted into an access device until the removable portion 1090 abuts the access device which may prevent the guide wire loading tool 1000 from advancing into the patient anatomy. In embodiments without a removable portion 1090, the guide wire loading tool 1000, with the stent delivery device, may be inserted into an access device until the expanded portion 1002 abuts the access device which may prevent the guide wire loading tool 1000 from advancing into the patient anatomy.

The stent delivery device may be advanced further, which may cause a distal portion of the guide wire loading tool 1000 to expand. For example, the expanded portion 1002 may expand as the stent delivery device passes through it. The stent delivery device may continue to advance until the device shield 1000 reaches a desired location with respect to the access device. For example, the desired location may include having the device shield 1000 positioned over a catheter shaft. The device shield 1000 may be grasped by the removable portion 1090. The practitioner may remove the device shield 1000 by retracting the removable portion 1090. In embodiments with a separation aperture 1092, removal of the device shield 1000 may include expanding the separation aperture 1092 while retracting the device shield 1000. Some embodiments of the device shield 1000 may be disposable.

Figure 11:
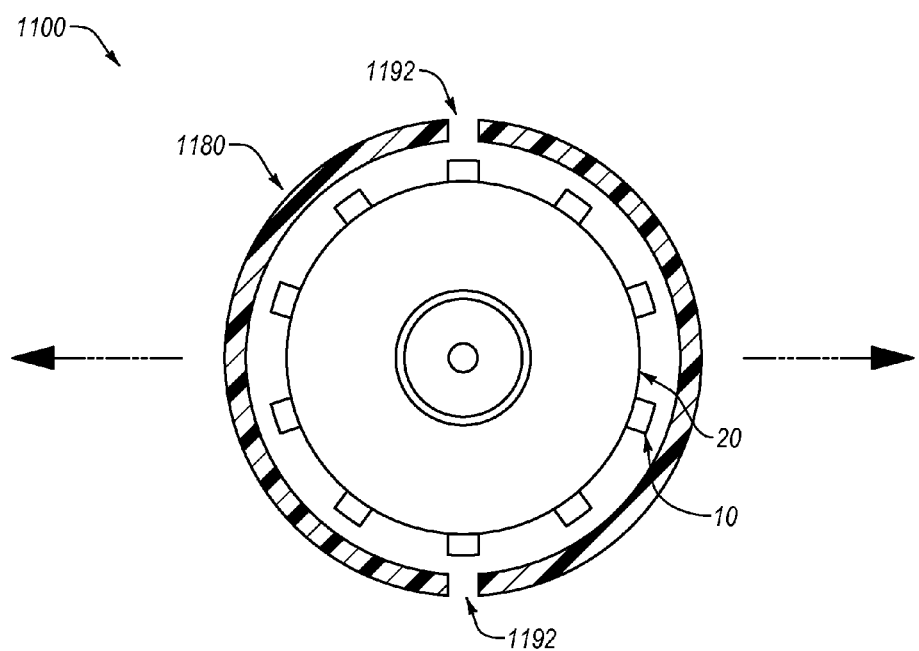
FIG. 11 illustrates an even further embodiment of a device shield for a medical device.

FIG. 11 illustrates a further embodiment of a device shield 1100. The device shield 1100 may incorporate other features from the other device shields described herein. For example, the device shield 1100 may include an expanded portion, such as expanded portions 102, 202, 1002, a limit element, such as limit elements 106, 206, 706, other elements, or combinations thereof.

The device shield 1100 may include an outer sheath 1180. The outer sheath 1180 may enclose at least a portion of the stent 10 and/or balloon 20. The outer sheath 1180 may include a separation aperture 1192, which may be similar to separation aperture 1092 shown in FIG. 11. The outer sheath 1180 may reduce significant tangential loads to the working element (i.e. stent 10 and/or balloon 20). For example, the separation aperture 1192 may facilitate removal in a generally radial and/or axial direction to reduce tangential loads. The reduction in tangential loads may reduce the potential amount of damage to the stent 10 and/or balloon 20 when the device shield 1100 is removed.

The stent 10 and/or balloon 20 may be transitioned from the device shield 1100 by removing the outer sheath 1180 from about the stent 10 and/or balloon 20. For example, as shown in FIG. 11, a tangential and/or other load may be applied to the outer sheath 1180 to facilitate splitting of the outer sheath 1180 and exposure of the stent 10 and/or balloon 20. This load may be applied at any time during the delivery of the stent 10.

The device shield 1110 may be positioned relative to an access device before removal of the outer sheath 1180. For example, the outer sheath 1180 may be removed after at least a portion of the stent 10 has been inserted into the access device. In other words, the device shield 1100 may be positioned such that it abuts the access device before applying a load to split the outer sheath 1180.

The stent 10 may be advanced into the access device relative to the removal of the outer sheath 1180. For example, as the outer sheath 1180 is split, the stent 10 may be simultaneously advanced into the access device. In another example, the stent 10 may be independently advanced into the access device.

Figure 12:
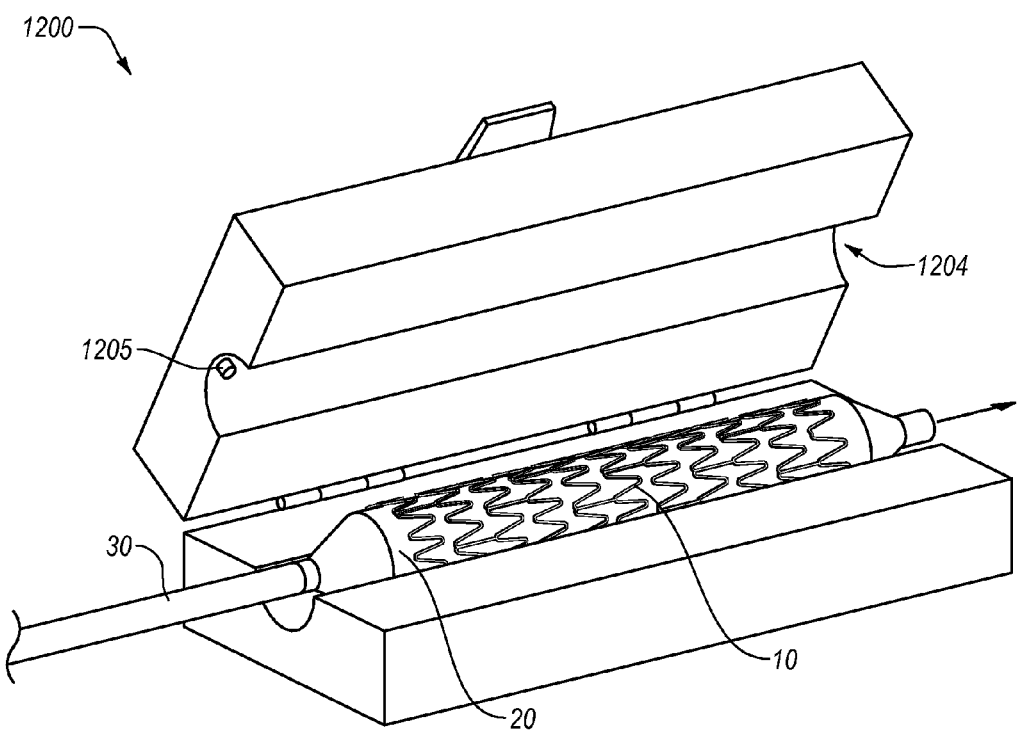
FIG. 12 illustrates a yet further embodiment of a device shield for a medical device.

FIG. 12 illustrates another embodiment of a device shield 1200. The device shield 1200 may incorporate other features from the other device shields described herein. For example, the device shield 1200 may include an expanded portion, a limit element, other elements described herein, or combinations thereof.

The device shield 1200 may include a storage portion 1204 that may be configured to store the stent and/or balloon (shown as stent 10 and balloon 20 above). In the present embodiment, the storage portion 1204 may include a retaining mechanism 1205 that may restrain longitudinal motion of the working element. The device shield 1200 may be split into an upper and lower portion, which may be connected by, for example, a hinge or other mechanism.

Figure 13A:
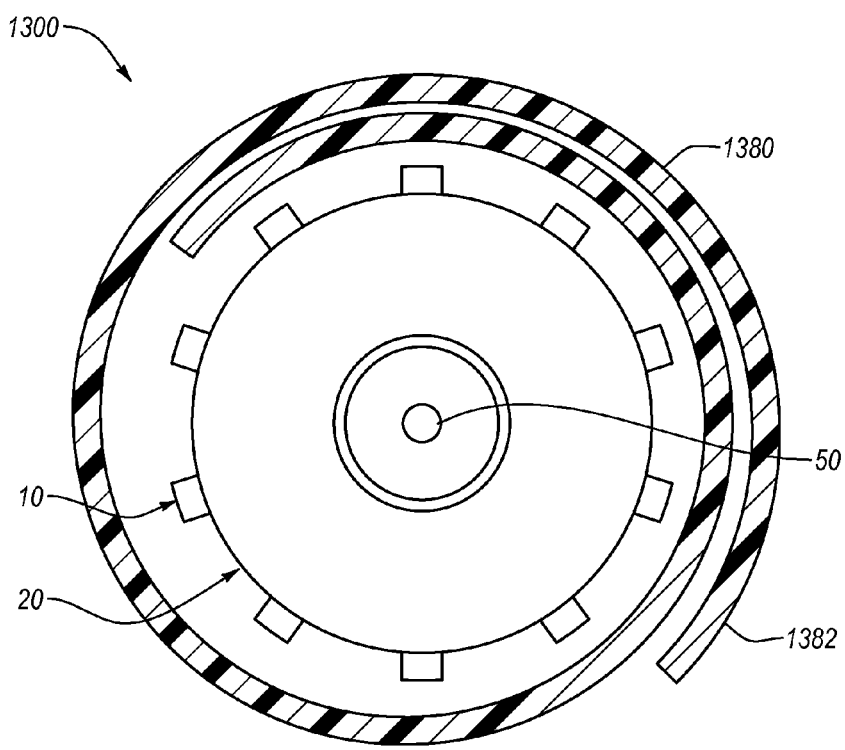
FIGS. 13A and 13B illustrate another embodiment of a device shield for a medical device.
Figure 13B:
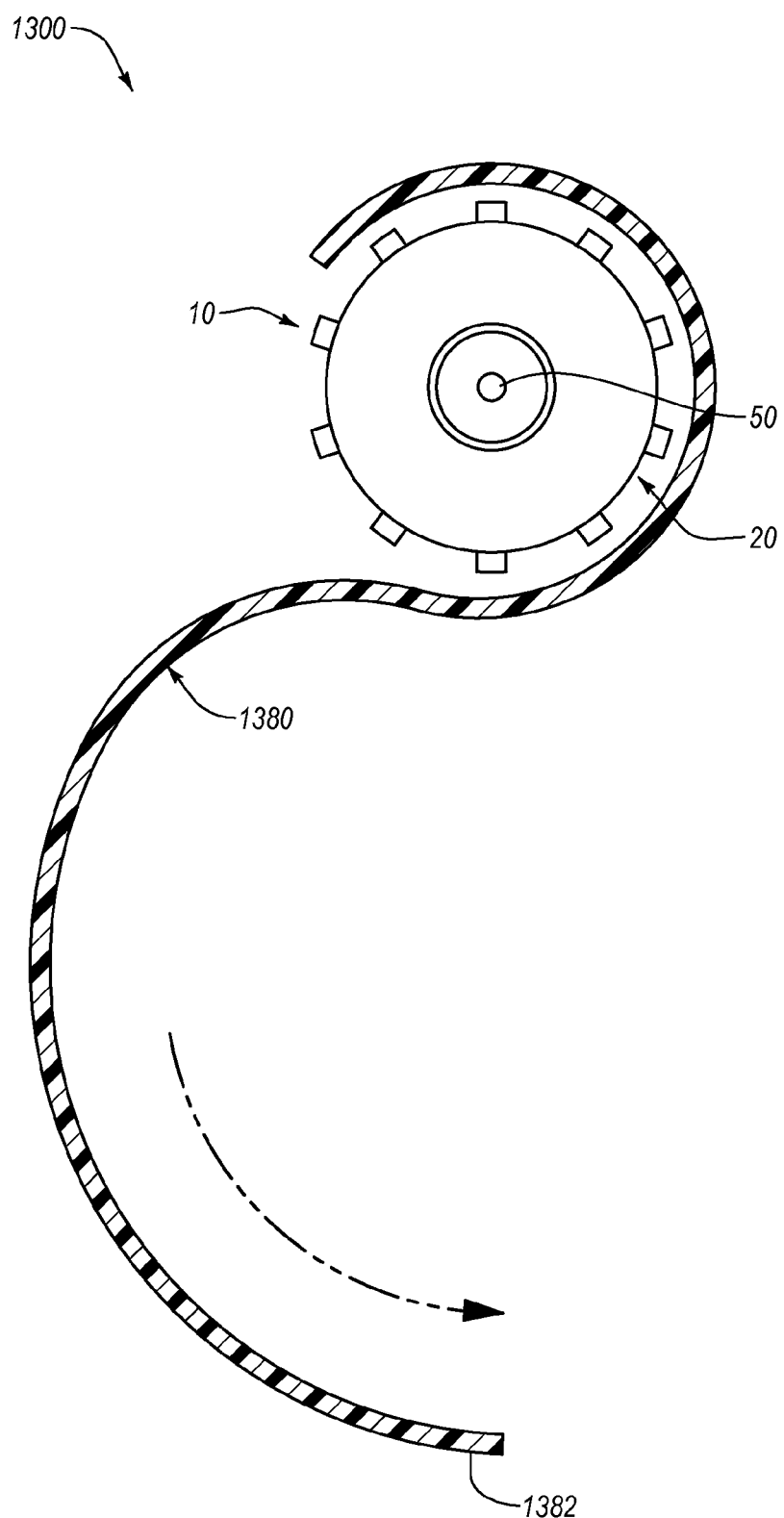

FIGS. 13A-13B illustrate another embodiment of a device shield 1300. The device shield 1300 may incorporate other features from the other device shields described herein. For example, the device shield 1300 may include an expanded portion, a limit element, other elements described herein, or combinations thereof.

The device shield 1300 may include an outer sheath 1380. The outer sheath 1380 may enclose at least a portion of the stent 10 and balloon 20. The outer sheath 1380 may overlap itself. By overlapping the sheath 1380, the stent 10 and/or balloon 20 may be generally protected from scratches and/or contamination. In addition, the outer sheath 1380 may reduce significant tangential loads to the working element (i.e. stent 10 and/or balloon 20). For example, as the sheath 1380 is removed, the overlapping feature may minimize loads to the working element.

In use, the outer sheath 1380 of the device shield 1300 can extend around a portion or the entirety of the outer surface of the working element (i.e. stent 10 and/or balloon 20) while a guide wire (not shown) is loaded into the working element. Once the guide wire has been loaded and the working element is ready to be removed from the device shield 1300, an end 1382 of the outer sheath 1380 that is positioned on the outside of device shield 1300 can be peeled away from the working element as shown in FIG. 13B. That is, the end 1382 can be pulled generally radially away from the working element such that the outer sheath 1380 is generally unwound from off of the working element. By unwinding the outer sheath 1380 off of or pulling the end 1382 generally radially away from the working element, the tangential loads experienced by the working element are reduced and/or minimized. Reducing and/or minimizing the tangential loads experienced by the working element can reduce the likelihood of damage to the working element.

Referring now to FIGS. 14-16B, a further alternative embodiment of a device shield 1400 is illustrated. The device shield 1400 is similar to the device shield 800 described herein and the guide wire loading device shown and described in U.S. Patent Publication No. 2006/0253048, published Nov. 9, 2006, entitled GUIDEWIRE LOADER APPARATUS AND METHOD, the disclosure of which is incorporated herein by reference in its entirety.

In the present embodiment, the device shield 1400 may have a split design. For example, the device shield 1400 may have an upper portion 1400*a* and a lower portion 1400*b*. In other embodiments, the device shield 1400 may be formed as a generally unitary body. For example, the majority of the device shield 1400 may be integrally formed.

Whether the device shield 1400 is formed in a split or unsplit configuration, the device shield 1400 may include a storage portion 1402 which may include a generally cylindrical body and/or generally cylindrical inner surface that may approximate the dimension of a stent delivery device, a balloon, and/or a crimped stent, individually and collectively identified as medical device 1404. In other embodiments, the upper portion 1400*a* and lower portion 1400*b* may differ. For example, only one of the upper portion 1400*a* or lower portion 1400*b* may include a storage portion 1402. The medical device can be similar or identical to the stent 10, the balloon 20, and/or the stent delivery device 30 illustrated in FIG. 2.

It will be appreciated that the device shield 1400, as well as the other device shields described herein, may be configured to receive other types of guide wire receiving devices therein. For instance, rather than receiving a stent and/or stent delivery device, the guide wire loading devices described herein may be adapted to receive a balloon catheter for performing angioplasty procedures and the like.

Figure 15:
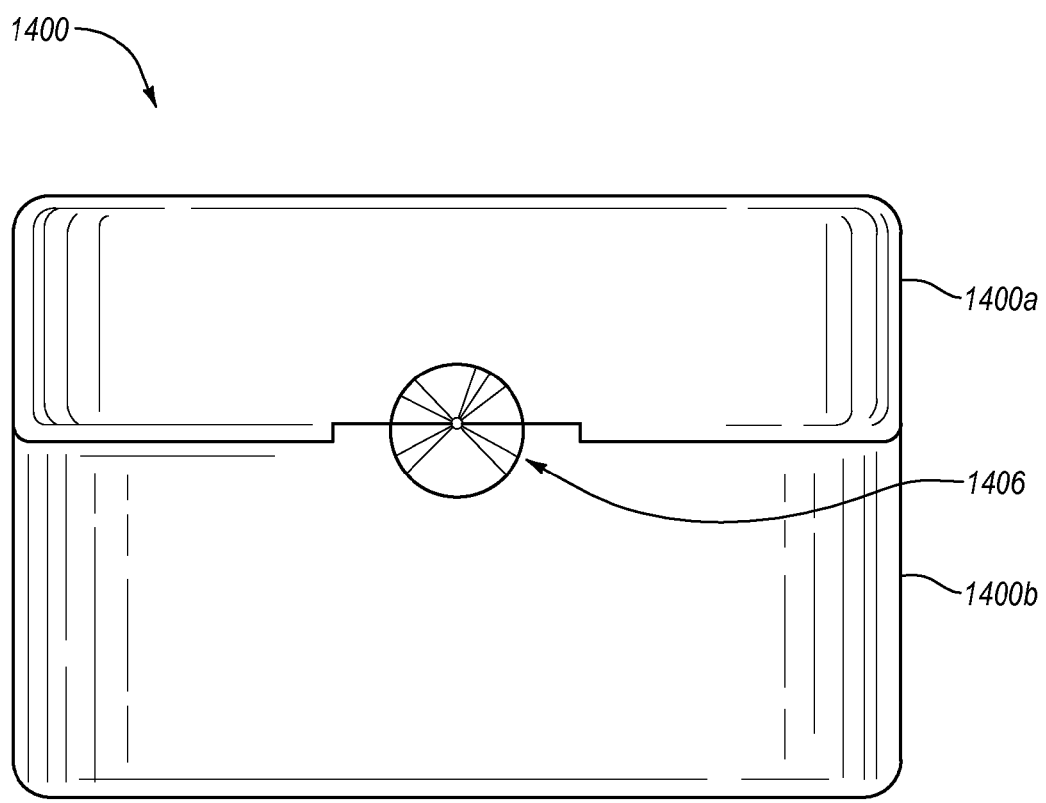
FIG. 15 illustrates an end view of the device shield of FIG. 14.
Figure 16A:
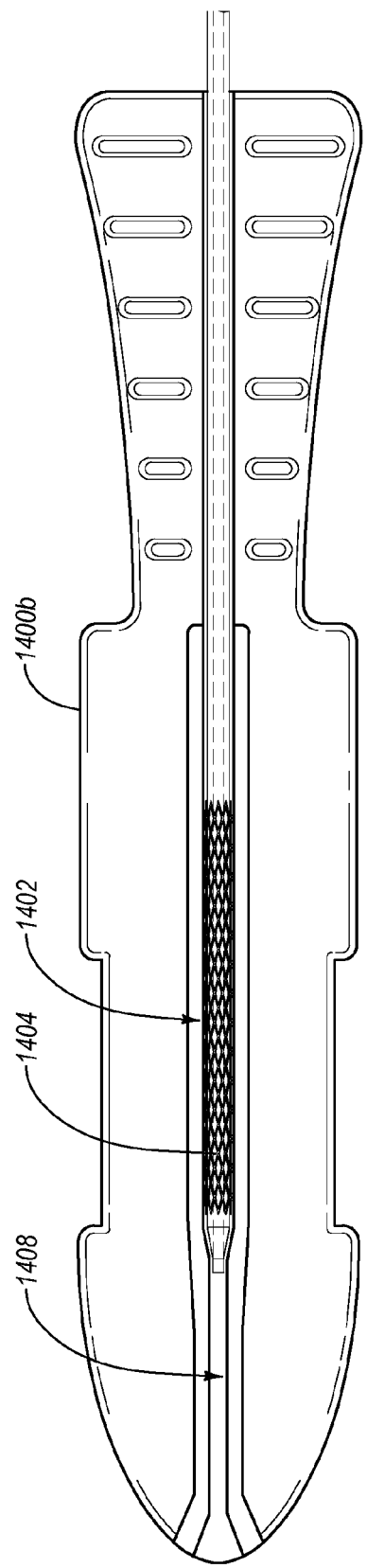
FIG. 16A illustrates a top view of the device shield of FIG. 14 with an upper portion removed therefrom.

As seen in FIG. 15, the upper portion 1400*a* and lower portion 1400*b* cooperate to define an insertion aperture 1406 near the distal end of device shield 1400. More specifically, each of the upper portion 1400*a* and the lower portion 1400*b* define a generally semi-cylindrical channel (the semi-cylindrical channel of the lower portion 1400*b* is shown in FIG. 16A at 1408) that form the insertion aperture 1406 when the upper portion 1400*a* and the lower portion 1400*b* are joined together. In other embodiments, the insertion aperture 1406 can be formed entirely by or within one of the upper portion 1400*a* and the lower portion 1400*b*.

As illustrated in FIG. 15, the insertion aperture 1406 may have a funneled portion that facilitates the direction of the guide wire into the medical device 1404 in a similar manner as the expanded portion 102 described above. In either case, a guide wire (not shown) may be inserted through the insertion aperture 1406 and into the medical device 1104. The upper portion 1400*a* and/or lower portion 1400*b* may be at least partially formed of clear plastic, which may facilitate verification of contents within the device shield 1400.

Figure 14:
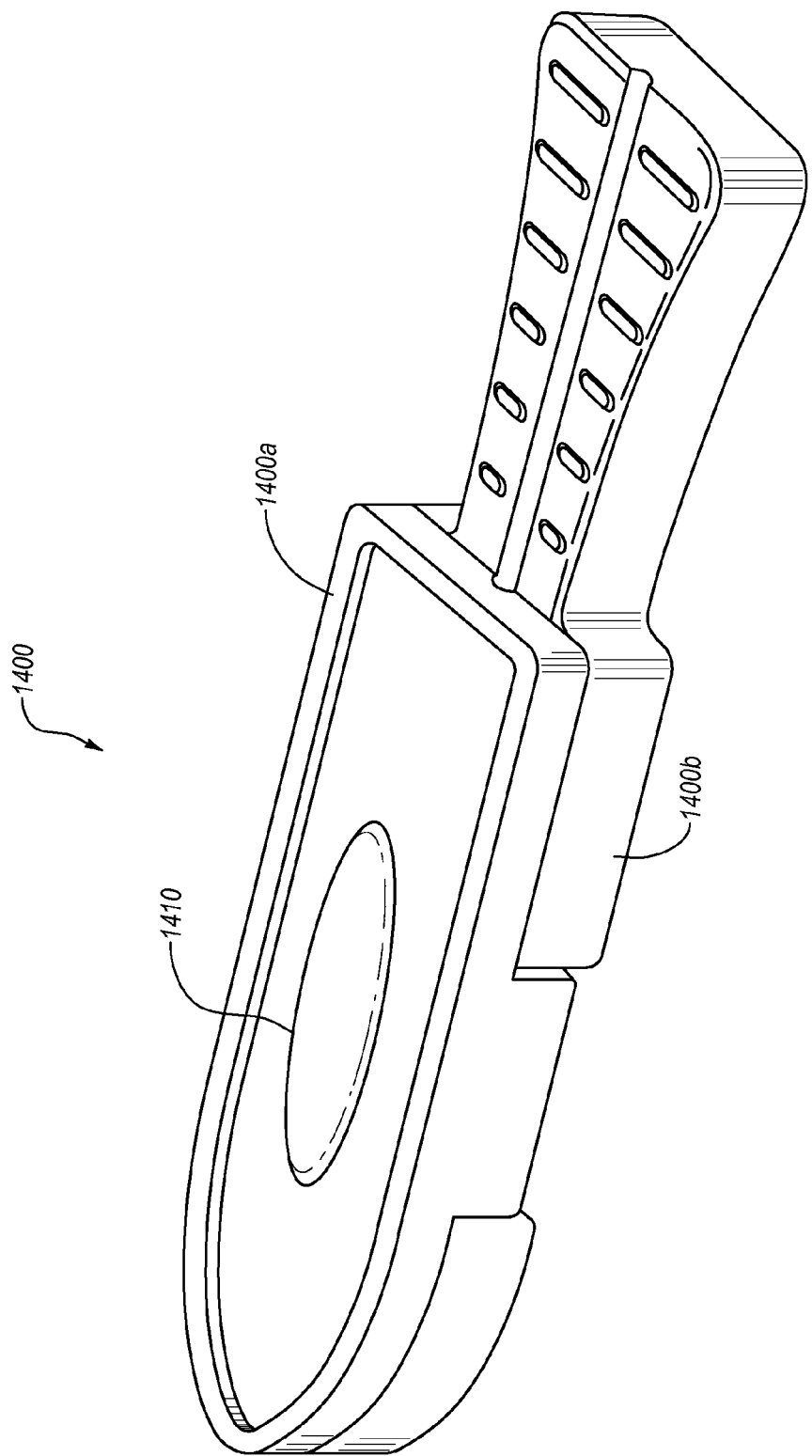
FIG. 14 illustrates a perspective view an another exemplary embodiment of a device shield for a medical device.
Figure 16B:
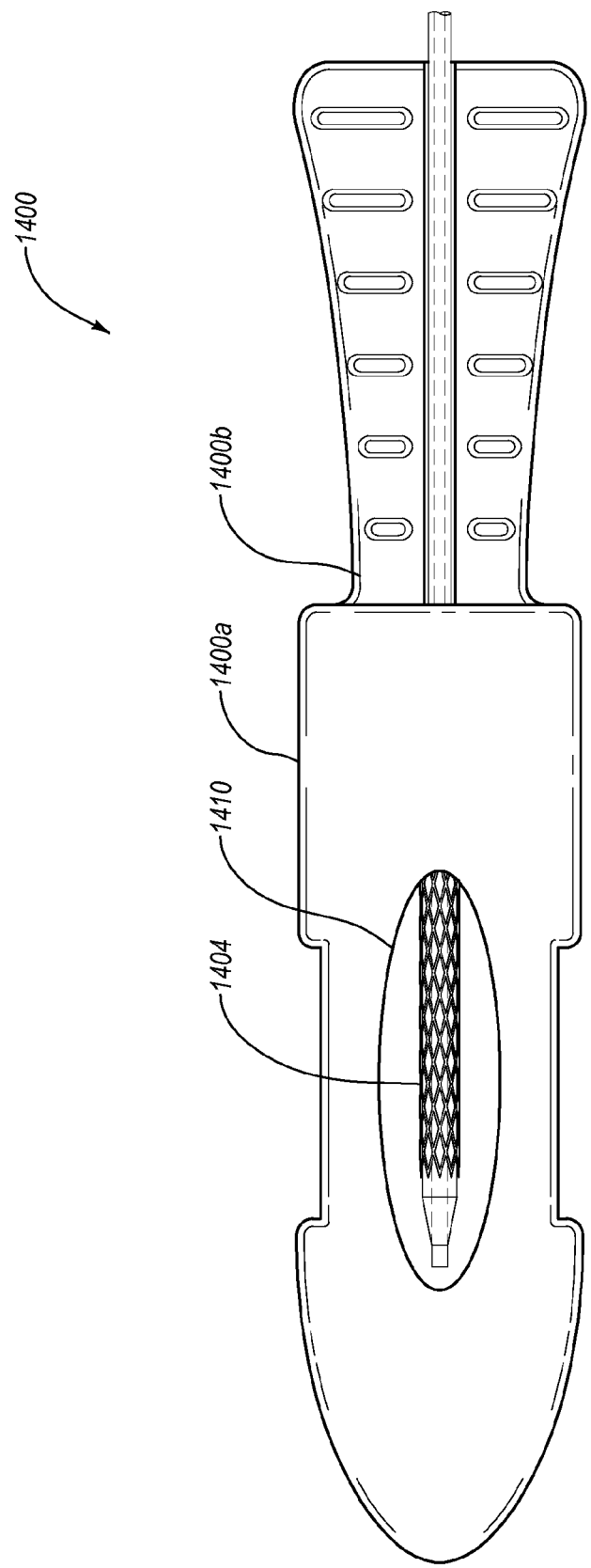
FIG. 16B illustrates a top view of the device shield of FIG. 14 with a magnification element in the upper portion.

With specific reference to FIGS. 14 and 16B, the guide wire loading device 1400 includes a magnification feature. In particular, a lens 1410 can be formed in or attached to the upper portion 1400*a* and/or the lower portion 1400*b*. The lens 1410 can be integrally molded on the upper portion 1400*a* and/or the lower portion 1400*b* by creating, with a transparent material, a bubble shape in at least one surface thereof. Forming the bubble in an appropriate convex shape causes the underlying device (e.g., the medical device 1404) to be magnified, as is well known in the field of optics.

The lens 1410 can also be formed in other ways while still providing the desired magnification benefits. By way of non-limiting example, a separate magnifying lens may be overmolded or bonded to the device shield 1400 to provide the desired magnification. Depending on the type of lens used and/or the material used to form the lens, the optical quality of the magnified image may be tailored as desired.

The lens 1410 feature allows the medical device 1404 that is positioned within the storage portion 1402 to be viewed under magnification. For example, medical device 1404 appears larger in FIG. 16B when viewed through lens 1410 as compared to the unmagnified view of the medical device 1410 shown in FIG. 16A when lens 1410 is not covering medical device 1410.

Magnification of the medical device 1404 can be beneficial for a number of reasons. For instance, magnification allows a physician to view the stent struts and determine whether they are bent, scratched, or otherwise damaged or compromised. Likewise, any coatings on the medical device 1404 may be more easily observed and potential scratches or other defects can be identified. Furthermore, in some embodiments, the lens 1410 may enable a physician to more easily view a lumen in the medical device (such as guide wire lumen 32 of stent delivery device 30 illustrated in FIG. 2). This can enable the physician to more easily insert a guide wire into medical device lumen without damaging the medical device. Thus, using the device shield 1400 with the lens 1410 enables a physician to inspect the condition of medical device 1404 to confirm the integrity of the medical device 1404 and maintain its condition prior to insertion into a patient.

It will be appreciated that variations of this design are possible that will allow the number of components to be reduced while retaining at least some of the main features and/or benefits. For example, the upper portion 1400*a* and lower portion 1400*b* may be associated with each other through a lateral living hinge or other connection along their edge. Several other embodiments may be contemplated that may incorporate the main features of the present disclosure.

Figure 17A:
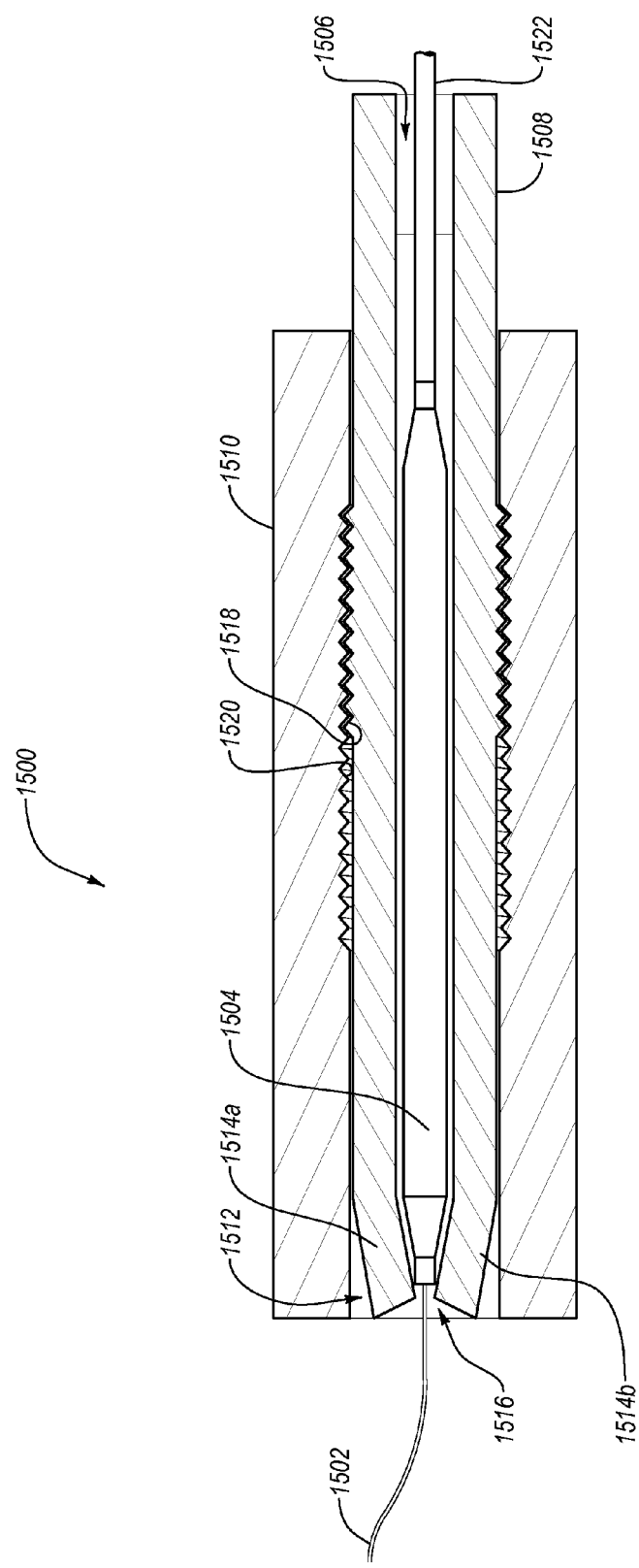
FIGS. 17A-17C illustrate still a further embodiment of a device shield that enables delivery of a medical device directly into an access device without exposure of the medical device.
Figure 17B:
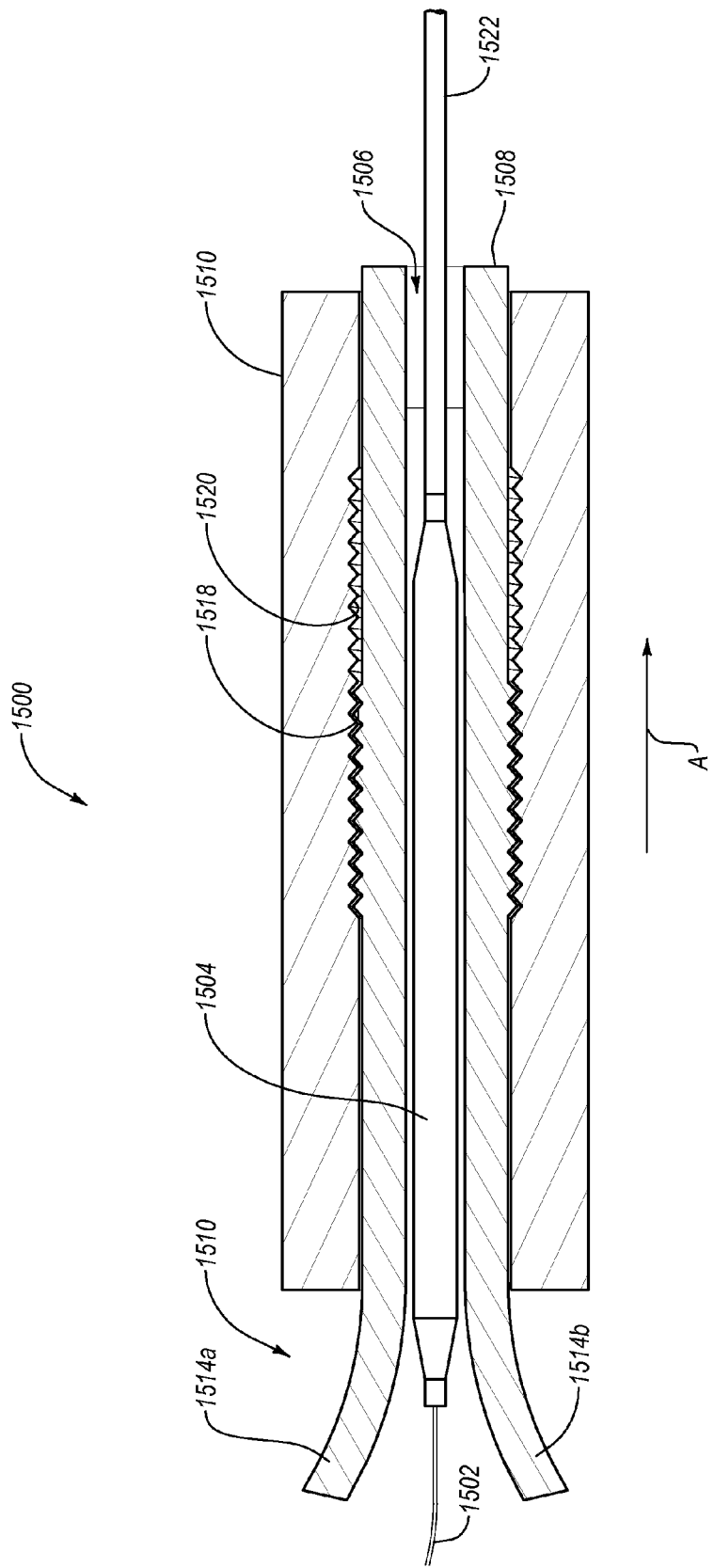
Figure 17C:
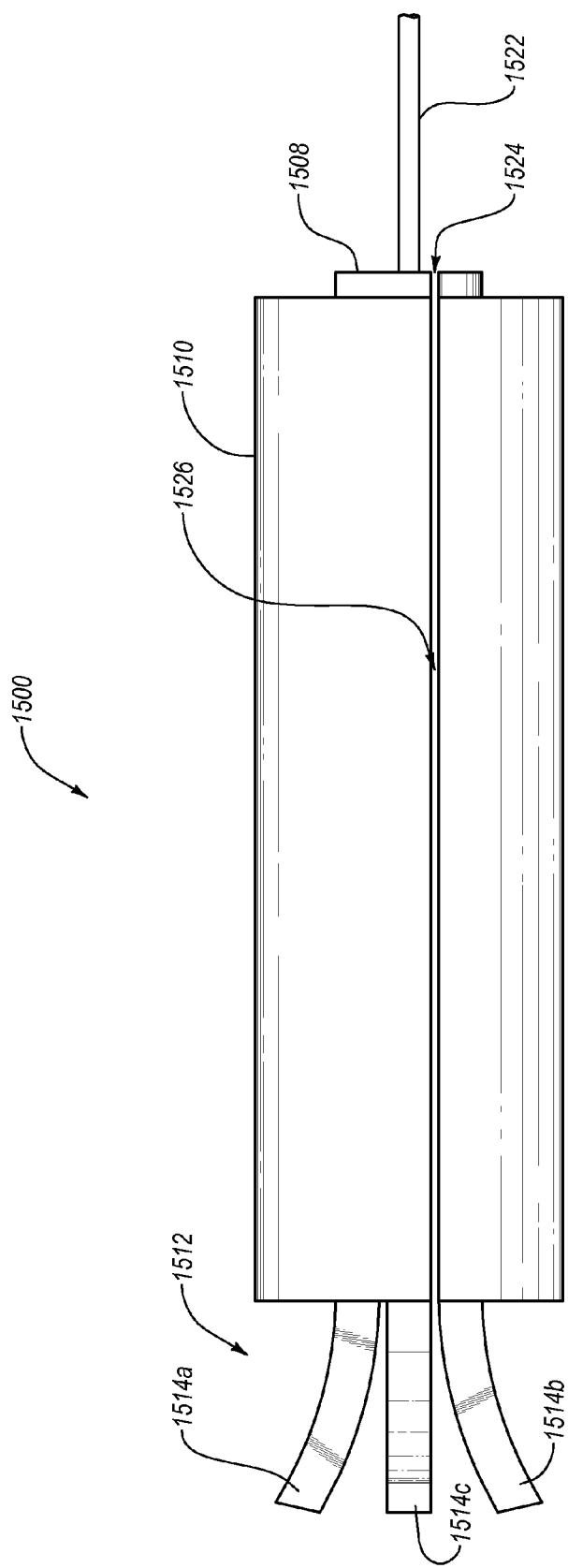

Attention is now directed to FIGS. 17A-17C, in which is illustrated another embodiment of a device shield 1500. The device shield 1500 allows a guide wire 1502 to be more easily inserted into a medical device 1504, or any other type of guide wire receiving device, by providing a tapered opening that directs the guide wire into the medical device 1504. Additionally, the device shield 1500 provides a mechanism for inserting the medical device 1504 directly into an access device, such as a guiding catheter or RHV, without exposing the medical device 1504 to the surrounding environment.

With reference to FIGS. 17A and 17B, the device shield 1500 is illustrated in cross-section with the medical device 1504 positioned within a storage portion 1506. The device shield 1500 has at least two parts: an inner sheath 1508 and an outer sheath 1510. The inner sheath 1508 is generally tubular in shape over at least a portion of its length and defines the storage portion 1506. The inner sheath 1508 also has a distal portion 1512 that includes flex sections 1514*a*-1514*n* that can either be flexed inward toward a central axis of the device shield 1500 (as shown in FIG. 17A) or allowed to recover to their naturally outward flexed shape (as shown in FIGS. 17B and 17C). As shown in the Figures, the outer sheath 1510 is generally tubular in shape and is received over the inner sheath 1508. The outer sheath 1510 is adapted to move along at least a portion of the length of the inner sheath 1508 for the reasons described below.

The outer sheath 1510 can engage or be mounted on the inner sheath 1508 in a variety of ways. As illustrated in FIGS. 17A and 17B, for instance, the outer surface of the inner sheath 1508 and the inner surface of the outer sheath 1510 have complimentary spiral threads 1518 and 1520. Threads 1518 and 1520 help secure the inner and outer sheaths 1508, 1510 together as well as allow for axial rotation of the outer sheath 1510 relative to the inner sheath 1508. As will be understood, the spiral nature of threads 1518, 1520 will cause the outer sheath 1510 to move along the length of the inner sheath 1508 as the outer sheath 1510 is axially rotated relative to the inner sheath 1508.

When the flex sections 1514*a*-1514*n* are moved inward as shown in FIG. 17A, they converge to form a tapered lumen 1516 at the distal end of the device shield 1500. The tapered lumen 1516 can be used when inserting the guide wire 1502 into the medical device 1504. More specifically, the inner surface of the tapered lumen 1516 defines a relatively large opening (compared to the lumen in the medical device 1504)

into which the end of the guide wire 1502 can be inserted. As the tapered lumen 1516 extends toward the storage portion 1506, the inner surface of the tapered lumen 1516 tapers to a smaller diameter that is approximately equal to the diameter of the lumen in the medical device 1504. Thus, as the guide wire 1502 is advanced further into the tapered lumen 1516, the tapering inner surface of the tapered lumen 1516 directs the end of the guide wire 1502 into the lumen of the medical device 1504. In this manner, the guide wire 1502 can be inserted into the medical device without scratching or otherwise damaging the medical device 1204 that is within the storage portion 1506.

In order to form the tapered lumen 1516, the flex sections 1514a-1514n are moved inward toward the central axis of the device shield 1500. The flex sections 1514a-1514n are moved inward with the aid of the outer sheath 1510. As the outer sheath 1510 moves over the distal portion 1512 of the inner sheath 1508, the outer sheath 1510 engages and compresses the flex sections 1514a-1514n inward, as shown in FIG. 17A.

After loading the guide wire 1502 into the medical device 1504 as described above, it may be desirable to enlarge the lumen 1516 to enable the medical device 1504 to be advanced over the guide wire 1502 and into an access device. More specifically, once the guide wire 1502 has been inserted into the medical device 1504, the device shield 1500 can be associated with an access device, such as an access catheter or RHV, and the lumen 1516 can be opened wide enough to allow the medical device 1504 to pass therethrough into the access device.

Referring to FIG. 17B, the opening of the tapered lumen 1516 will be discussed in more detail. The tapered lumen 1516 can be enlarged by retracting the outer sheath 1510 relative to the inner sheath 1508 in the direction indicated by arrow A. In the illustrated embodiment, the retraction of the outer sheath 1510 is accomplished by rotating the outer sheath 1510 relative to the inner sheath 1508, which allows it to be moved in the direction of arrow A due to the spiral threads 1518, 1520. As the outer sheath 1510 is moved in the direction of arrow A, flex sections 1514a-1514n are uncovered and allowed to move to their naturally outward flexed shape, as shown in FIGS. 17b and 17C. As the flex sections 1514a-1514n flex outwardly, the lumen 1516 widens enough to allow the medical device 1504 to pass therethrough.

Alternatively, in other embodiments, the outer sheath 1510 may be associated with or mounted on the inner sheath 1508 in other ways. By way of non-limiting example, the outer sheath 1510 may simply be sized so as to be slidably mounted on the inner sheath 1508. In this configuration, the outer sheath 1510 could simply be retracted off of the flex sections 1514a-1514n by sliding or pulling back on the outer sheath 1510 in the direction of arrow A. When the outer sheath 1510 is refracted, the flex sections 1514a-1514n of the inner sheath 1508 will return to their natural outwardly flexed configuration, which will cause the lumen 1516 to open as described above.

With the guide wire 1502 loaded into the medical device 1504 and the lumen 1516 opened up, the device shield 1500 can be associated with an access device (not shown). For instance, the flex sections 1514a-1514n can be aligned with or inserted into an opening in an access device, such as an access catheter or RHV. Once the device shield 1500 is properly positioned relative to the access device, the medical device 1504 can be advanced into the access device for deployment into the patient. Notably, the device shield 1500 allows for both the insertion of the guide wire 1502 into the medical device 1504 without the risk of damaging the medical device 1504, and the advancement of the medical device 1504 into an access device without exposing the medical device 1504 to the surrounding environment where the medical device 1504 could be contaminated.

After the medical device 1504 is inserted into the access device, it may be desirable for the device shield 1500 to be removed from the catheter body 1522. This may be accomplished in a variety of ways, but one exemplary method of doing so is described here. Referring to FIG. 17C, a side view of the device shield 1500 shows that the inner sheath 1508 has a slot 1524 in its sidewall that runs axially along the length of the inner sheath 1508. Similarly, the outer sheath 1510 has a slot 1526 in its sidewall that runs axially along the length of the outer sheath 1510. As noted above, the outer sheath 1510 can be axially rotated relative to the inner sheath 1508. Axial rotation of the outer sheath 1510 relative to the inner sheath 1508 can align the slots 1524, 1526. When the slots 1524, 1526 are aligned, the catheter body 1522 can be removed from the device shield 1500 through the aligned slots 1524, 1526. In the illustrated embodiment, which includes the complimentary threads 1518, 1520 on the inner and outer sheaths 1508, 1510, the inner and outer sheaths 1508, 1510 and the threads 1518, 1520 are arranged so that the slots 1524, 1526 are aligned when the outer sheath 1510 is refracted, as shown in FIG. 17C. Thus, the device shield 1500 can be removed off the catheter body 1522 and discarded.

Other embodiments of device shield 1500 may be created by one of skill in the art. By way of non-limiting example, there is no need for the slots 1524, 1526 to align if the outer sheath 1510 can be retracted fully off of the inner sheath 1508 and each sheath 1508, 1510 is independently removed over the catheter body 1522. Thus, device shield 1500 allows the guide wire to be inserted into a medical device without damaging the medical device and allows the medical device to be delivered directly into an access device without the medical device being exposed to the surrounding environment in a significant manner.

Figure 18:
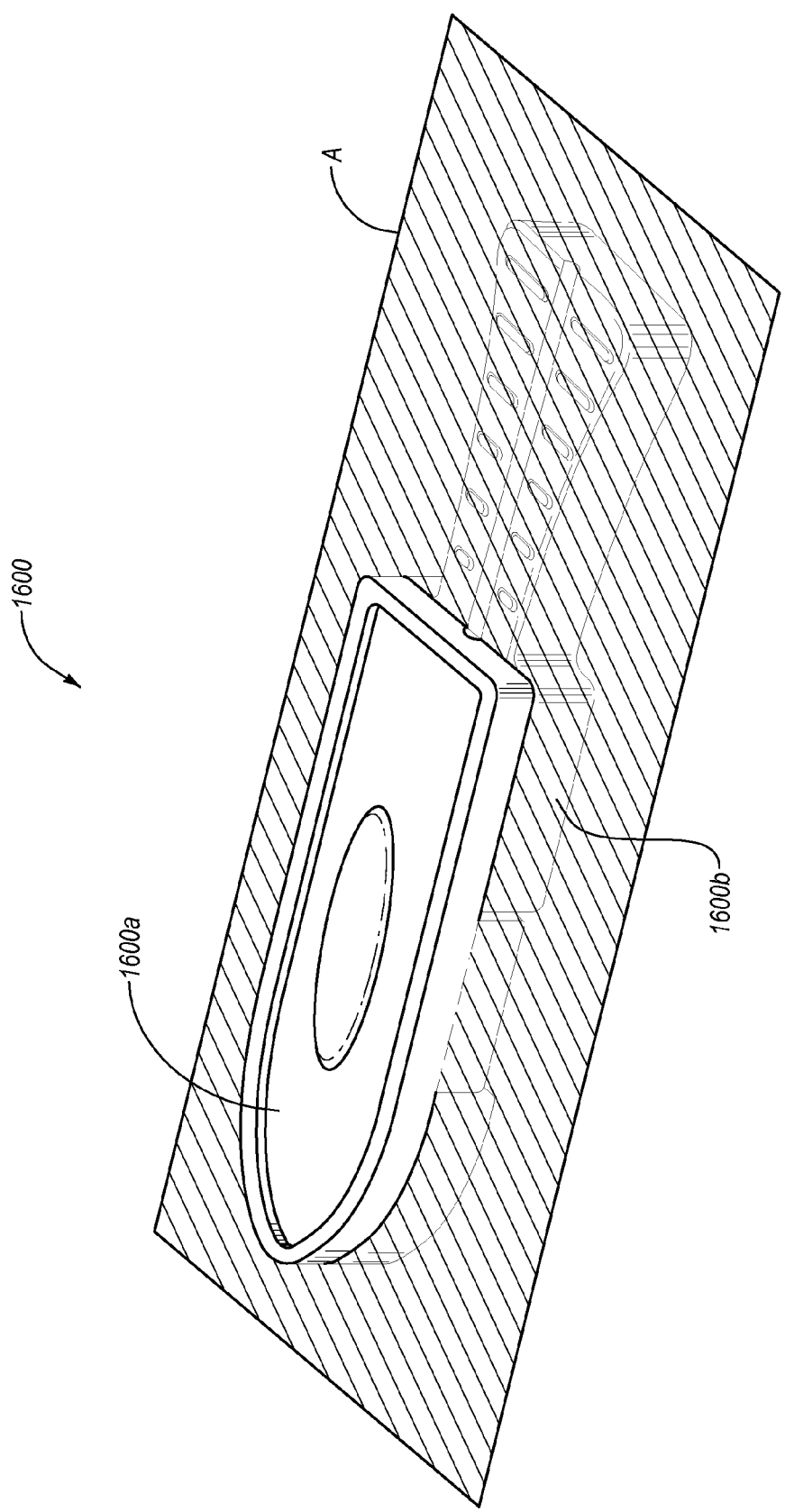
FIGS. 18 and 19A-19B illustrate an embodiment of a device shield that is adapted to fold or refold a balloon.
Figure 19A:
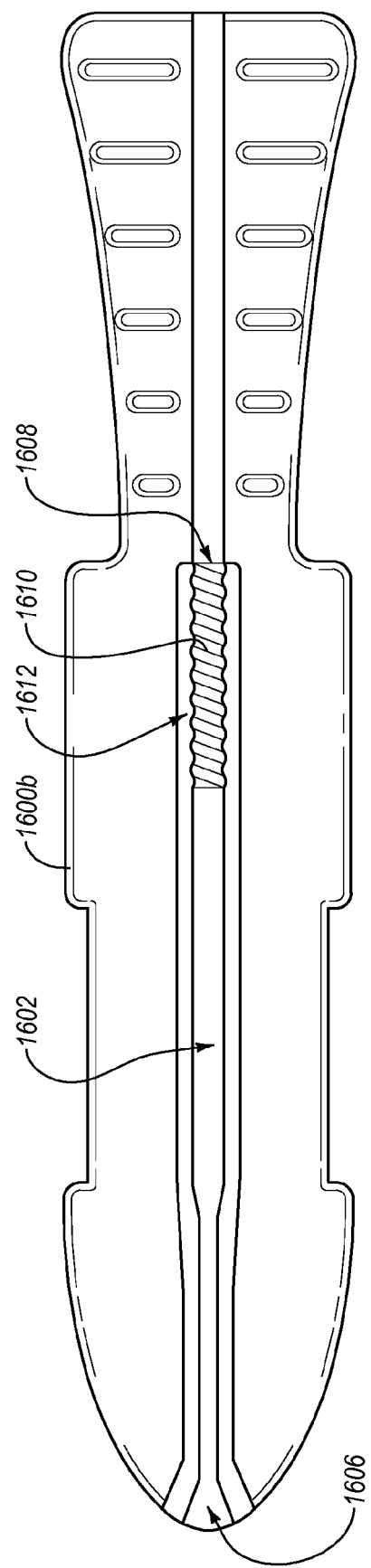
Figure 19B:
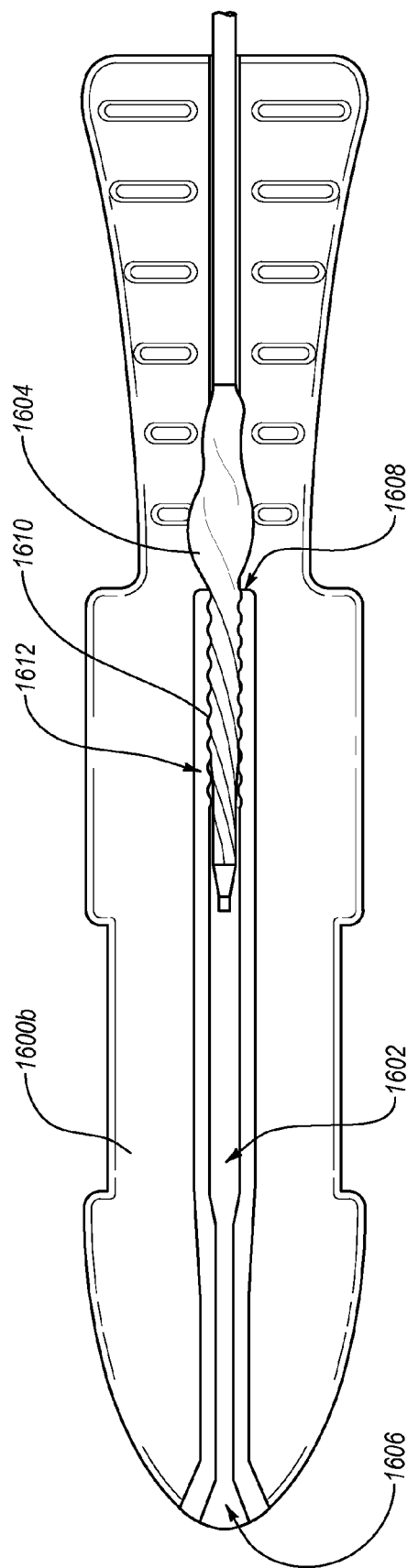

Turning now to FIGS. 18-19B, there is illustrated another exemplary embodiment of a device shield 1600. The device shield 1600 is similar to the guide wire loading devices 800 and 1400 discussed above, as well as the guide wire loading device shown and described in U.S. Patent Publication No. 2006/0253048, mentioned above. Similar to the other device shields described herein, the device shield 1600 enables a guide wire to be easily inserted into a medical device without the risk of scratching or otherwise damaging the medical device. In addition, the device shield 1600 also enable an unfolded balloon to be easily and quickly refolded without the risk of contaminating the balloon so that the balloon can be inserted into a patient in a clean and ready manner.

In the present embodiment, the device shield 1600 has a split design. Specifically, the device shield 1600 has an upper portion 1600a and a lower portion 1600b. In FIG. 18, sectional plane A is shown extending between the major portions of the upper and lower portions 1600a, 1600b. In other embodiments, the device shield 1600 may be formed as a generally unitary body. For example, the majority of the device shield 1600 may be integrally formed.

Whether the device shield 1600 is formed in a split or unsplit configuration, the device shield 1600 may include a storage portion 1602 which may include a generally cylindrical body and/or generally cylindrical inner surface that may approximate the dimension of a balloon 1604. In other embodiments, the upper portion 1600a and lower portion 1600b may differ. For example, only one of the upper portion 1600a or lower portion 1600b may include a storage portion 1602.

As seen in FIGS. 19A and 19B, device shield 1600 includes a lumen 1606 at the distal end thereof. The lumen 1606 can be used when inserting a guide wire (not shown) into the balloon 1604. More specifically, the inner surface of the lumen 1606 defines a relatively large opening (compared to the lumen in the balloon 1604) into which the end of the guide wire can be inserted. As the lumen 1606 extends toward the storage portion 1602, the inner surface of the lumen 1606 tapers to a smaller diameter that is approximately equal to the diameter of the lumen in the balloon 1604. Thus, as the guide wire is advanced further into the lumen 1606, the tapering inner surface of the lumen 1606 directs the end of the guide wire into the lumen of the balloon 1604. In this manner, the guide wire can be inserted into the balloon 1604 without scratching or otherwise damaging the balloon 1604. The lumen 1606 can be formed cooperatively by the upper portion 1600a and the lower portion 1600b when the upper and lower portions 1600a, 1600b are connected together. In other embodiments, the lumen 1606 can be formed entirely by or within either the upper portion 1600a or the lower portion 1600b.

In addition to facilitating insertion of a guide wire into the balloon 1604, device shield 1600 also facilitates the folding or refolding of the balloon 1604. The folding or refolding of the balloon 1604 can be accomplished either as the balloon 1604 is inserted into the storage portion 1602 or as the balloon 1604 is deployed from the storage portion 1602.

The folding or refolding of the balloon 1604 is achieved with grooves that are formed in the device shield 1600 at the end of the of storage portion 1602 opposite from the lumen 1606. Referring to FIG. 19A, there is shown a sectional view of the device shield 1600 looking down on plane A (i.e., a top view of the lower portion 1600b with upper portion 1600a removed). In this Figure it can be seen that near the proximal portion of the storage portion 1602, there is a semi-circular channel 1608 having spiral grooves 1610 formed in the lower portion 1600b. While not illustrated, a corresponding grooved channel is also formed in the upper portion 1600a. As will be understood, when the upper and lower portions 1600a, 1600b are joined together, the corresponding grooved channels cooperate to form a rifled portion 1612, or a channel having one or more spiraling grooves. The rifled portion 1612 may be formed during injection molding of the upper and lower portions 1600a, 1600b, regardless of whether the upper and lower portions are formed individually or as an integral piece.

The rifled portion 1612 is adapted to fold or refold the balloon 1604 as the balloon 1604 is inserted into or deployed from the device shield 1600 through the rifled portion 1612. More specifically, as illustrated in FIG. 19B, when an unfolded balloon 1604 is inserted into the storage portion 1602 through the rifled portion 1612, the unfolded balloon 1604 will be deformed by the grooves 1610 in the rifled portion 1612 such that one or more folds are created by the spiral grooves 1610. Further advancement of the balloon 1604 causes the folds to take a spiral form, which in combination with the reduction of profile creates a refolded balloon 1604. Thus, by simply inserting and advancing an unfolded balloon 1604 through the rifled portion 1612, the balloon 1604 will fold and rest within the storage portion 1602 of the device shield 1600. Once the folded balloon 1604 is so positioned within the storage portion 1602, a guide wire may be loaded into the balloon 1604 as described above and the balloon 1604 may be deployed as intended.

In an alternative embodiment, a balloon 1604 could be placed in the storage portion 1602 while the balloon is unfolded. After inserting a guide wire into the unfolded balloon 1604, the balloon 1604 could be deployed (i.e., passed into an access device, for example) through the rifled portion 1612. As the unfolded balloon 1604 passes through the rifled portions 1612, the spiral grooves 1610 in the rifled portion 1612 create one or more folds in the balloon 1604 such that the balloon 1604 is folded as the balloon 1604 exits the rifled portion 1612.

It will be appreciated that the rifled portion 1612 may be formed with one or more rifling grooves, depending on the number of folds that are desired. For example, two grooves would create two folds in the balloon, three folds would form three folds, and so on. Furthermore, the grooves in the rifled portion may be axially aligned instead of being spiraled grooves. Axially aligned grooves will create folds that align axially with the balloon. Further, a reduction in profile in the device shield will cause a reduction in profile of the balloon as it is advanced, thereby causing the folds to compress to a lower profile.

It yet another embodiment, the grooves in the rifled portion 1612 may have an axially aligned portion and a spiral portion. Including bother axially aligned and spiraled grooved portions would allow the folds in the balloon to first be formed axially and then to be rotated to reach a lower profile. It will be appreciated that a number of different configurations and groove profiles may likewise be used to fold or refold an expanded balloon prior to insertion within a patient's body. Thus, the device shield 1600 both allows for the insertion of a guide wire into a balloon without risk of damaging the balloon as well as being able to easily fold or refold the balloon prior to insertion into a patient.

The various embodiments are described herein with respect to a stent and/or balloon. The present disclosure may also be used with other medical devices. For example, the device shield may be used with lumen filters, closure devices, graft materials, other medical devices, or combinations thereof. Medical devices of all types are advanced over guide wires. In addition, various stents may be used with the present disclosure. For example, drug eluting stents, bare metal stents, bioabsorbable stents, stents of varying sizes and/or structures, other stents, or combinations thereof with or without their accompanying balloons or other deployment devices may be used. Furthermore, self-expanding stents may be used with embodiments of the present disclosure. For example, the storage portions (described as 104, 204, 704 above) may store a self-expanding stent without a balloon. In another example, the self-expanding stent may be stored within a catheter that may be stored within a storage portion.

III. Methods for Delivering a Medical Device

An embodiment of a method for delivering a medical device into a patient's body may include using any of the devices described above, in order to reduce and/or prevent contamination and/or damage of a medical device and/or delivery device surface prior to device insertion within the patient anatomy. The method may include packaging a device with a protective covering. After opening the surrounding package in a procedural environment, such as the catheter lab, a guide wire may be inserted into the device through the protective covering and the covering will be advanced with the enclosed device into, or adjacent to, an access device, such as an RHV.

A mechanism may be actuated on the protective covering to allow the device to be inserted into the anatomy through the access device, although it is also possible in some embodiments to use a protective covering that requires no actuation before device insertion. Following insertion, the protective covering may be removed and/or discarded. It will be appreciated that according to this method, the surface of the device that is disposed within the protective covering may be shielded from contamination by particulates within the surrounding environment until it is inserted through the access device or at the very least the device may be shielded from contamination or damage until just before insertion through the access device. As shown in FIGS. 1A-1C, protecting the medical device from contamination and/or damage from prior to opening the packaging around the medical device to insertion or just prior to inserting the device into the patient's vasculature may improve clinical outcomes.

In another embodiment, a method for delivering a medical device into a patient body includes (1) positioning an introducer apparatus in the patient body and (2) positioning at least a portion of a device shield into the introducer apparatus. In one embodiment, the device shield includes (a) a housing that includes a medical device and at least a portion of a medical device delivery apparatus associated with the medical device, and (b) a limit element having a first position configured to constrain the medical device and/or the portion of the medical device delivery apparatus associated with the medical device.

The method for delivering a medical device into a patient body further includes (3) transitioning the limit element to a second position, wherein the second position is configured to permit delivery of the medical device into the patient body, and (4) delivering the medical device from the device shield and into the patient body via the introducer apparatus.

In one embodiment, the method for delivering a medical device into a patient body further includes inserting a guide wire into a guide wire lumen of the medical device delivery apparatus prior to positioning the device shield into the introducer apparatus.

In another embodiment, positioning at least the portion of the device shield into the introducer apparatus triggers an actuator for transitioning the limit element from the first position to the second position. In another embodiment, the method for delivering a medical device into a patient body further includes removing a retaining member from the housing to transition the limit element from the first position to the second position. In yet another embodiment, the method for delivering a medical device into a patient body further includes tearing or peeling at least a portion of the housing away from the medical device to transition the limit element from the first position to the second position.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A device shield for minimizing contamination of or damage to a medical device having an expandable portion, comprising:
   a housing configured to maintain a medical device within the housing such that exposure of the medical device to the environmental particulates and the damage is minimized, the housing having a storage portion formed in the housing at a location disposed between a proximal end and a distal end of the housing; and
   a limit element formed with the housing and being pivotally received within the storage portion of the housing, the limit element having a first position and a second position, the limit element being configured in the first position to constrain the expansion of the expandable portion of the medical device relative to the housing and to ensure that the medical device is not exposed to the damage and the environmental particulates, and the limit element configured in the second position to permit movement of the medical device relative to the housing once the risk of exposure to the environmental particulates and the damage is minimized, the limit element including a hinged proximal end, the hinge being transverse to a longitudinal axis of the housing, and a distal end being pivotal towards and away from the longitudinal axis in the direction to constrain and release the medical device a retaining member slidably associated with the housing and configured to extended over the limit element and a portion of the housing constraining the expandable portion of the medical device and maintain the limit element in the first position to ensure that the medical device, with the expandable portion, is not exposed to the damage and the environmental particulates.

2. The device shield of claim 1, wherein the first position is configured to prevent movement of the medical device out of the housing and the second position is configured to permit movement of the medical device out of the housing.

3. The device shield of claim 2, wherein the medical device is a stent and further comprising a medical device delivery apparatus.

4. The device shield of claim 3, wherein the housing is configured to store the medical device and to permit insertion of the medical device into a body without substantial exposure to an air environment surrounding the body and/or without exposure to hand contact.

5. The device shield of claim 4, the housing further comprising an expanded portion configured to direct a guide wire into a guide wire lumen of the medical device delivery apparatus maintained within the housing.

6. The device shield of claim 5, wherein the limit element is configured to preserve at least one specified dimension of the medical device and/or the medical device delivery apparatus while in the first position.

7. The device shield of claim 6, wherein the limit element is molded to conform to a shape of the medical device and at least a portion of the medical device delivery apparatus.

8. The device shield of claim 1, wherein the limit element is coupled to an actuator configured to actuate a movement of the limit element from the first position to the second position.

9. The device shield of claim 1, wherein the retaining member is removably disposed around the housing such that the retaining member can be removed from the housing for transitioning the limit element from the first position to the second position.

10. A device shield for minimizing contamination of a medical device, including an expandable portion, from environmental particulates and damage to the medical device, comprising:
    a shaped housing configured to maintain a medical device and at least a portion of a medical device delivery apparatus associated with the medical device within the housing such that exposure of the medical device to the environmental particulates and the damage is minimized, the shaped housing having a storage portion at a location disposed between a proximal end and a distal end of the housing;
    a limit element formed with the shaped housing and being pivotally received within the storage portion of the shaped housing, the limit element being configured to constrain the medical device and/or the portion of a medical device delivery apparatus associated with the medical device in at least one dimension, a hinged proximal end of the limit element connected to the shaped housing and extending transversely to a longitudinal axis of the housing and a distal end of the limit element being distal the proximal end of the housing and the hinged proximal end and being pivotal towards and away from the longitudinal axis in the direction to constrain and release the medical device;

a retaining member slidably associated with the housing and configured to extend over the limit element and a portion of the housing constraining the expandable portion of the medical device and maintain the limit element in the first position to ensure that the medical device, with the expandable portion, is not exposed to the damage and the environmental particulates; and an outlet configured for introducing the medical device into a body of a patient once the risk of exposure to the environmental particulates and the damage is minimized.

11. The device shield of claim 10, wherein the limit element is transitionable from the first constraining position to a second releasing position.

12. The device shield of claim 11, wherein the limit element comprises a first half gate and a second half gate.

13. The device shield of claim 12, wherein the first and second half gates collectively constrain the medical device and/or the portion of a medical device delivery apparatus associated with the medical device in a radial dimension when the first and second half gates are in the first constraining position.

14. The device shield of claim 10, wherein the limit element is configured to preserve at least one specified dimension of the medical device and/or the medical device delivery apparatus.

15. The device shield of claim 14, wherein the limit element is shaped to conform to a shape of the medical device and/or a shape of the portion of a medical device delivery apparatus associated with the medical device.

16. The device shield of claim 10, wherein the limit element further comprises a shaped portion configured to direct a guide wire into a guide wire lumen of the medical device delivery apparatus.

17. The device shield of claim 10, wherein the retaining member is disposed around the housing in a first arrangement configured to maintain the limit element in the first position to ensure that the medical device is not exposed to the damage and the environmental particulates and the retaining member is slidable to a second arrangement configured for transitioning the limit element from the first position to the second position once the risk of exposure to the environmental particulates and the damage is minimized.

18. The device shield of claim 10, wherein the outlet is configured to mate with an introducer sheath and/or a rotating hemostatic valve (RHV) for introducing the medical device into a body of a patient.

19. A kit for minimizing contamination of a medical device, including an expandable portion, from environmental particulates and damage to the medical device, comprising:

a medical device;

a medical device delivery apparatus; and a device shield, including:

a housing configured to maintain the medical device and at least a portion of the medical device delivery apparatus associated with the medical device within the housing such that exposure of the medical device to the environmental particulates and the damage is minimized, the housing including a proximal end, a distal end, a storage portion spaced apart from the proximal end and the distal end, and a lumen having a longitudinal axis and extending into and from the storage portion, the storage portion being disposed between the proximal end and the distal end of the housing; and a limit element formed with the housing and being configured to receive and constrain the expansion of the expandable portion of the medical device in the housing in at least one dimension such that exposure of the medical device to the environmental particulates and the damage is minimized, the limit element extending into the storage portion through the housing in a direction transverse to the longitudinal axis and being pivotally coupled to the housing at a hinged proximal end of the limit element, which is transverse to the longitudinal axis, a distal end of the limit element being pivotal towards and away from the longitudinal axis in the direction to constrain and release the medical device a retaining member slidably associated with the housing and configured to extend over the limit element and a portion of the housing constraining the expandable portion of the medical device and maintain the limit element in the first position to ensure that the medical device, with the expandable portion, is not exposed to the damage and the environmental particulates.

20. The kit of claim 19, wherein the medical device is a stent.

21. The kit of claim 20, wherein the stent is supported by a balloon.

22. The kit of claim 19, wherein the medical device delivery apparatus is a catheter.

23. The kit of claim 19, wherein the limit element is shaped to conform to a shape of the medical device and/or a shape of the portion of the medical device delivery apparatus associated with the medical device.

* * * * *